(12) United States Patent
Zhang et al.

(10) Patent No.: US 8,317,730 B2
(45) Date of Patent: Nov. 27, 2012

(54) ROBOTIC REHABILITATION APPARATUS AND METHOD

(75) Inventors: Li-Qun Zhang, Wilmette, IL (US);
Hyung-Soon Park, Rockville, MD (US);
Yupeng Ren, Chicago, IL (US)

(73) Assignee: Rehabtek LLC, Wilmette, IL (US)

( * ) Notice: Subject to any disclaimer, the term of this patent is extended or adjusted under 35 U.S.C. 154(b) by 385 days.

(21) Appl. No.: 12/527,389

(22) PCT Filed: Feb. 15, 2008

(86) PCT No.: PCT/US2008/054148
§ 371 (c)(1),
(2), (4) Date: Aug. 14, 2009

(87) PCT Pub. No.: WO2008/101205
PCT Pub. Date: Aug. 21, 2008

(65) Prior Publication Data
US 2010/0016766 A1  Jan. 21, 2010

Related U.S. Application Data

(60) Provisional application No. 60/901,788, filed on Feb. 16, 2007.

(51) Int. Cl.
*A61B 5/103* (2006.01)
*A61B 5/117* (2006.01)
*A61H 1/00* (2006.01)
*A61H 1/02* (2006.01)
*A61H 5/00* (2006.01)
*A61H 7/00* (2006.01)
*A61H 19/00* (2006.01)

(52) U.S. Cl. .............. 600/595; 600/587; 601/5; 601/33; 601/84

(58) Field of Classification Search .................. 600/587, 600/595; 601/5, 23, 24, 25, 26, 33, 40, 84; 602/20–23; 482/5–7, 44–50; 128/878, 879, 128/881
See application file for complete search history.

(56) References Cited

U.S. PATENT DOCUMENTS 7,125,388 B1   10/2006   Reinkensmeyer et al.
(Continued)

FOREIGN PATENT DOCUMENTS

WO   2008101205 A2   8/2008
(Continued)

OTHER PUBLICATIONS

O'Malley et al., "The RiceWrist: A Distal Upper Extremity Rehabilitation Robot for Stroke Therapy", Proceedings of IMECE, Chicago, Illinois, USA, Nov. 5-10, 2006, p. 1-10.*
(Continued)

*Primary Examiner* — Max Hindenburg
*Assistant Examiner* — Devin Henson

(57) ABSTRACT

This patent describes an 8+2 degrees of freedom (DOF) intelligent rehabilitation robot capable of controlling the shoulder, elbow, wrist and fingers individually and allowing functional arm movements with accompanying trunk and scapular motions. The rehabilitation robot uses the following integrated rehabilitation approach: 1) it has unique diagnostic capabilities to determine patient-specific multiple joint and/or multiple DOF biomechanical and neuromuscular changes; 2) it stretches the stiff joints/DOFs under intelligent control to loosen up the specific stiff joints and to reduce excessive cross-coupling torques/movements between the specific joints/DOFs, which can be done based on the above diagnosis for subject-specific treatment; 3) the patients practice voluntary reaching and some functional tasks to regain/improve their motor control capability, which can be done after the stretching loosened up the stiff joints; and 4) the outcome will be evaluated quantitatively at the levels of individual joints, multiple joints/DOFs, and the whole arm.

21 Claims, 18 Drawing Sheets

U.S. PATENT DOCUMENTS 7,618,381 B2 * 11/2009 Krebs et al. .................. 601/5
2006/0106326 A1 5/2006 Krebs et al.
2006/0293617 A1 12/2006 Einav et al.

FOREIGN PATENT DOCUMENTS

WO 2008101205 A3 8/2008

OTHER PUBLICATIONS

Kodek et al., "An analysis of static and dynamic joint torques in elbow flexion-extension movements", Simulation Modelling Practice and Theory 11, May 14, 2003, p. 297-311.*

* cited by examiner

ROBOTIC REHABILITATION APPARATUS AND METHOD

CROSS-REFERENCE TO RELATED APPLICATIONS

This application claims priority to PCT/US2008/054148 filed Feb. 15, 2008, and U.S. Provisional Patent Application No. 60/901,788 filed Feb. 16, 2007.

RELATED ART

The present invention is in the field of physical rehabilitation equipment.

BACKGROUND OF THE INVENTION

Field of the Invention

The present invention relates to a device for diagnosing, exercising, training, and evaluating human limbs. More specifically, to a robotic device that allows rehabilitation including precise diagnosis throughout the workspace of the limbs, stretching a limb under intelligent control, training the limb movement through voluntary exercises, and performing outcome evaluation.

Spasticity, contracture, muscle weakness, and motor impairment are commonly seen following stroke. The several symptoms are closely related to each other and are major factors contributing to disabilities in patients post stroke. The hypertonus and reflex hyperexcitability disrupt the remaining functional use of muscles, impede motion, and may cause painful muscle spasms. Loss of muscle control, weakening and fatiguing of muscles, lack of appropriate joint movement, prolonged spasticity and associated painful muscle spasms may be accompanied by structural changes of muscle fibers and connective tissue, which may result in a reduction in joint range of motion (ROM) and lead to a clinical contracture, joint deformity, and motor impairment.

Several stereotypical patterns of limb deformity with multiple joints involved are commonly seen in patients with neurological impairments, including adducted/internally rotated shoulder, flexed elbow, pronated forearm, flexed wrist, clenched fist, foot drop, and abnormal gait motion. There is a strong need to treat the deformed/hypertonic limbs and multiple involved joints simultaneously on a frequent basis to reduce spasticity/contracture and increase mobility.

For most patients post stroke, physical therapy is the cornerstone of the rehabilitation process. Physical therapy is important and effective in treating persons with hypertonic/deformed limbs. A physical therapist uses physical modalities, functional training, exercises, and one-on-one manual manipulation of the stroke patient's body with the intent of reducing spasticity and contracture and restoring movement function. However, the effects may not be long lasting, partly due to the limited and sometime infrequent therapy a patient can receive. Practically, the manual stretching is laborious and the outcome is dependent on the experience and subjective "end feeling" of the therapists. For both the patients and therapists, there is a need for a device that can stretch and mobilize the joints precisely, reliably, and effectively.

For effective treatment, it is very important to accurately diagnose limb impairments at multiple joints and multiple degree of freedom (DOF) at each joint (e.g., shoulder horizontal abduction/adduction, flexion/extension, and upper arm axial rotation at the shoulder). Motor impairments in patients post stroke affect the multiple joints of the limb simultaneously. In terms of joint biomechanical properties, patients may develop spastic hypertonia and reduced ROM at multiple joints with abnormal coupling among the joints and with multiple DOFs at each joint. In terms of voluntary control, patients post stroke may loose independent movements of individual joints and coordination among the joints. There is a strong need to diagnose the multi-joint/DOF pathological changes and then treat the joints in well coordinated ways. However, it is not practical for a clinician to evaluate the increased resistance and abnormal couplings at the multiple joints and multi-DOFs simultaneously and quantitatively. More accurate and comprehensive diagnosis/evaluation is needed using a novel robotic device and use the information obtained to guide subsequent treatment/training.

A number of rehabilitation robotic devices have been used to exercise the involved joints and reduce joint spasticity/contractures. See, U.S. Pat. No. 6,599,255 B2. For example, the continuous passive motion (CPM) device is widely used in clinics and in patients' home to move a joint within a pre-specified movement range, to prevent postoperative adhesion and reduce joint stiffness. Advanced robot-aided devices have also been developed to evaluate limb impairment quantitatively, and to assist and guide patient's hand to reach a target in the limb workspace to enhance neurorehabilitation following brain injury. However, existing devices like the CPM machine move the limb at a constant speed between two preset joint positions. When it is set within the flexile part of the ROM, the passive movement does not usually stretch into the extreme positions where contracture/spasticity is significant. On the other hand, setting a CPM machine too aggressively may risk injuring the joint because the machine controls the joint position or velocity without incorporating the resistance torque generated by the soft tissues. There is a need for a device that can safely stretch the joint(s) to the extreme positions with accurate control of the resistance torque and stretching velocity. Furthermore, there is a need to follow up the strenuous passive stretching with training of active movement and to evaluate the impairment and rehabilitation outcome quantitatively and objectively.

SUMMARY OF THE INVENTION

The invention is a new intelligent rehabilitation robot capable of controlling all joints simultaneously, which help to achieve effective stroke rehabilitation based on the following features incorporated: 1) it has unique diagnostic capabilities for individual patients including information on which joints and which DOFs are impaired, what are the abnormal couplings, and whether the problem is due to passive muscle properties or active control capabilities; 2) based on the diagnosis, it stretches the hypertonic/deformed limb of the patients post stroke under intelligent control to loosen up the specific stiff joint(s) or to break up abnormal couplings between joints/DOFs so that the CNS can potentially control the relevant muscles and limb movement more effectively; 3) with the stiff joints loosed up, the patients perform voluntary exercise to regain/improve their motor control capability; 4) the outcome is evaluated quantitatively at the levels of individual joints, multiple joints/DOFs, and the whole limbs.

The present invention satisfies the need for the therapy of limbs with impairment through a multi-step integrated rehabilitation approach: diagnosing neuromuscular and biomechanical impairments in limb functions, performing physical therapy including passive stretching and voluntary movement exercises, and evaluating the outcome quantitatively (FIG. 1).

The present invention further satisfies the need for a limb and joint therapeutic device that is precise and accurate. Furthermore, the invention satisfies the need for a device that can stretch the limb or joint(s) under intelligent control and allow the human subject move his/her limb freely or help the movement with assistance.

Finally, the device satisfies the need for quantitative and objective measurements of the impairments in terms of the biomechanical and neuromuscular changes for diagnosis and outcome evaluations.

According to the embodiments of the present invention, there is a limb and joint therapeutic device for use by both clinicians and patients, whether at home or at a clinic. The limb and joint therapeutic device has a limb support, the limb support securing a limb such that the limb is rotatable with respect to a joint. The device has motors and motor shafts, the motors and shafts rotating the joints at a variable velocity. A controller controls the velocity or resistance torque in different control modes. In the intelligent stretching mode, the controller controls the stretching velocity at each joint based on the joint resistance torque measurement. In the active exercise mode, the controller controls the multiple joints involved based on the diagnosis by the device and/or by the clinician.

The above advantages, features and aspects of the present invention are readily apparent from the following detailed description, appended claims and accompanying drawings.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

COMPONENT LIST

Figure 1:
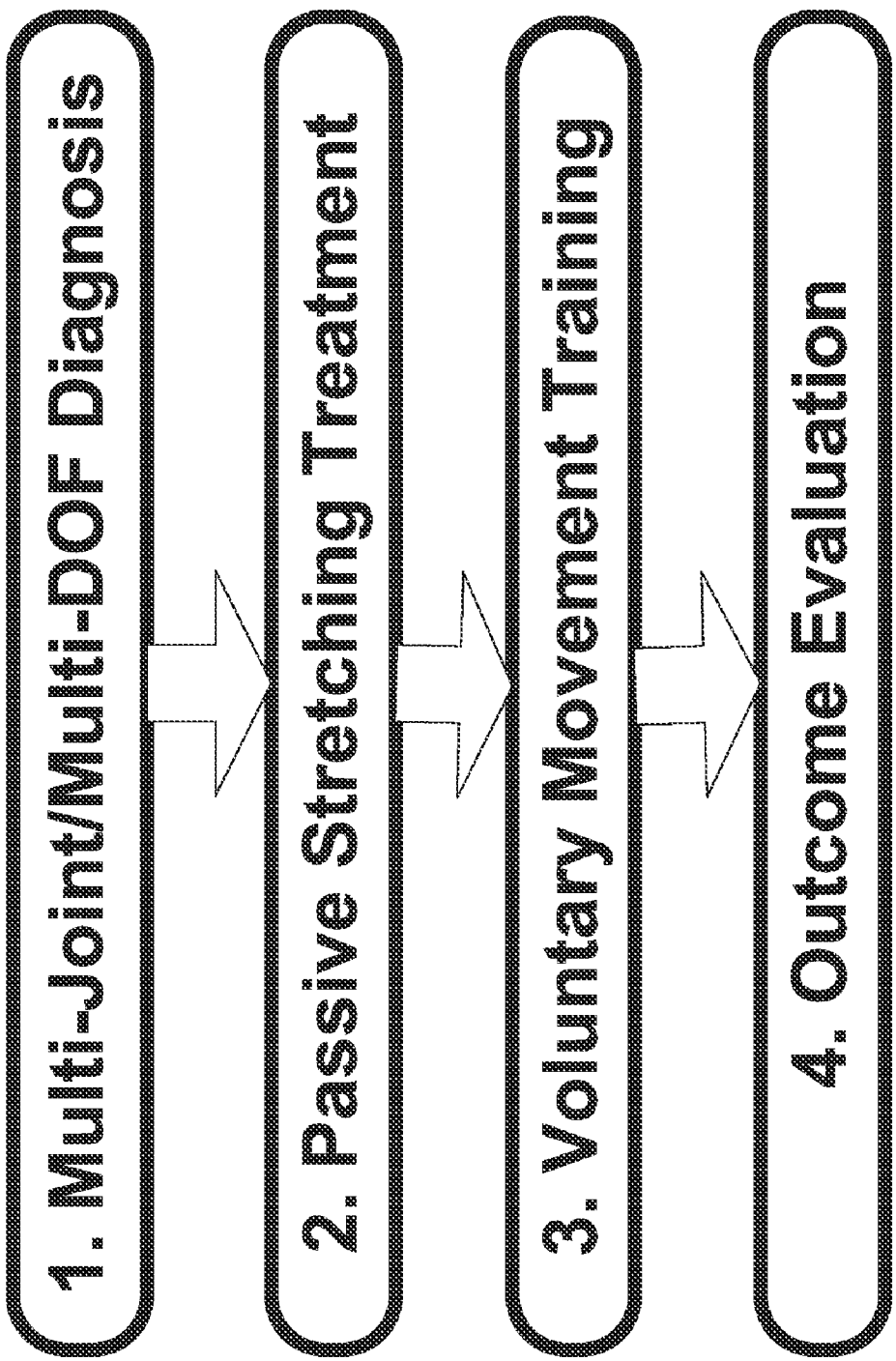
FIG. 1 is a flowchart describing the multi-step integrated rehabilitation program proposed in the invention.

12 Vertical Disp. Actuator
14 Shoulder Flexion Motor
16 Shoulder Horizontal Abduction Motor
18 Shoulder Platform (X, Y, Z Displacement)
20 Shoulder Horizontal Abduction
22 Arm Rotation
24 Circular Guide
26 Forearm Supination
28 Wrist Flexion
30 MCP Finger Flexion
32 Hand strap
34 Finger Motor
36 Finger Torque Sensor
38 Wrist multi-axis force sensor
40 Wrist Motor
42 Forearm Length Adjustment
44 Supination Motor
46 Elbow Motor
48 Elbow Multi-Axis Force Sensor
50 Elbow Flexion
52 Arm Length Adjustment
54 Arm rotation motor
56 Shoulder multi-axis force sensor
58 Shoulder Flexion
60 Vertical Guide
62 Horizontal X-Y Guides
64 Linear Actuator for vertical motion (Z direction)
66 Supporter for Gravity Compensation
68 Linear Motion Guide in Vertical Direction
70 Glenohumeral Joint
72 X-Y motion
74 Z direction (Scapular Elevation/Depression)
76 Motor for Shoulder H. Ab/Adduction
78 Motor for Shoulder Flexion/Extension
80 Cable for driving Shoulder Flexion
82 Cable for driving Shoulder Int./Ext. Rotation
84 Circular guide for shoulder Int./Ext. Rotation
86 Motor for Shoulder Int./Ext. Rotation
88 6DOF Force/Torque sensor
90 Pulley for changing direction of cable tension
92 Shoulder Horizontal Link
94 Cable Tensioners
96 Shaft 1A
98 Shaft 1B
100 Shaft 2A
102 Shaft 2B
104 Drum 2
106 Drum 1
108 Motor for Elbow Flexion/Extension
110 6 DOF force/torque Sensor
112 Circular Guide
114 Forearm links
116 Motor for Forearm Sup./Pron.
118 Cable driving Forearm Sup./Pron.
120 Drum 2
122 Drum 1
124 Cable driving elbow joint
126 Cable Tensioner
128 Shaft 1B
130 Shaft 1A
132 6 DOF force/torque sensor
134 Motor for hand opening/closing
136 Two bar linkage
138 Torque sensor for MCP joint
140 Cable driven bevel gear
142 Motor for wrist flexion/extension

DETAILED DESCRIPTION OF THE PREFERRED EMBODIMENTS

The following description of the preferred embodiment(s) is merely exemplary in nature and is in no way intended to limit the invention, its application, or uses.

Embodiments of the invention provide techniques for robotic rehabilitation using the four-step integrated protocol including multi-joint/multi-DOF diagnosis, intelligent passive stretching, voluntary movement training, and outcome evaluation.

A. Patient-Specific Diagnosis of the Passive and Active Biomechanical Changes at the Joints in the Limbs.

In the passive mode, the multi-joint device moves the joints of the impaired limb throughout the ROMs both simultaneously and individually under precise control with the multi-axis torques and positions measured at the joints simultaneously. In the active mode, the patient is asked to move the impaired joints individually and the multiple joints of the limb simultaneously for functional movements such as reaching and walking, with the multi-joint and multi-DOF dynamic properties measured at every joint simultaneously. Multi-joint and multi-DOF analysis is done on the data from the passive and active movements to diagnose the multi-joint biomechanical changes in the impaired limb during certain tasks, which is directly useful in guiding rehabilitation of the impaired limb in the subsequent aims.

Figure 2:
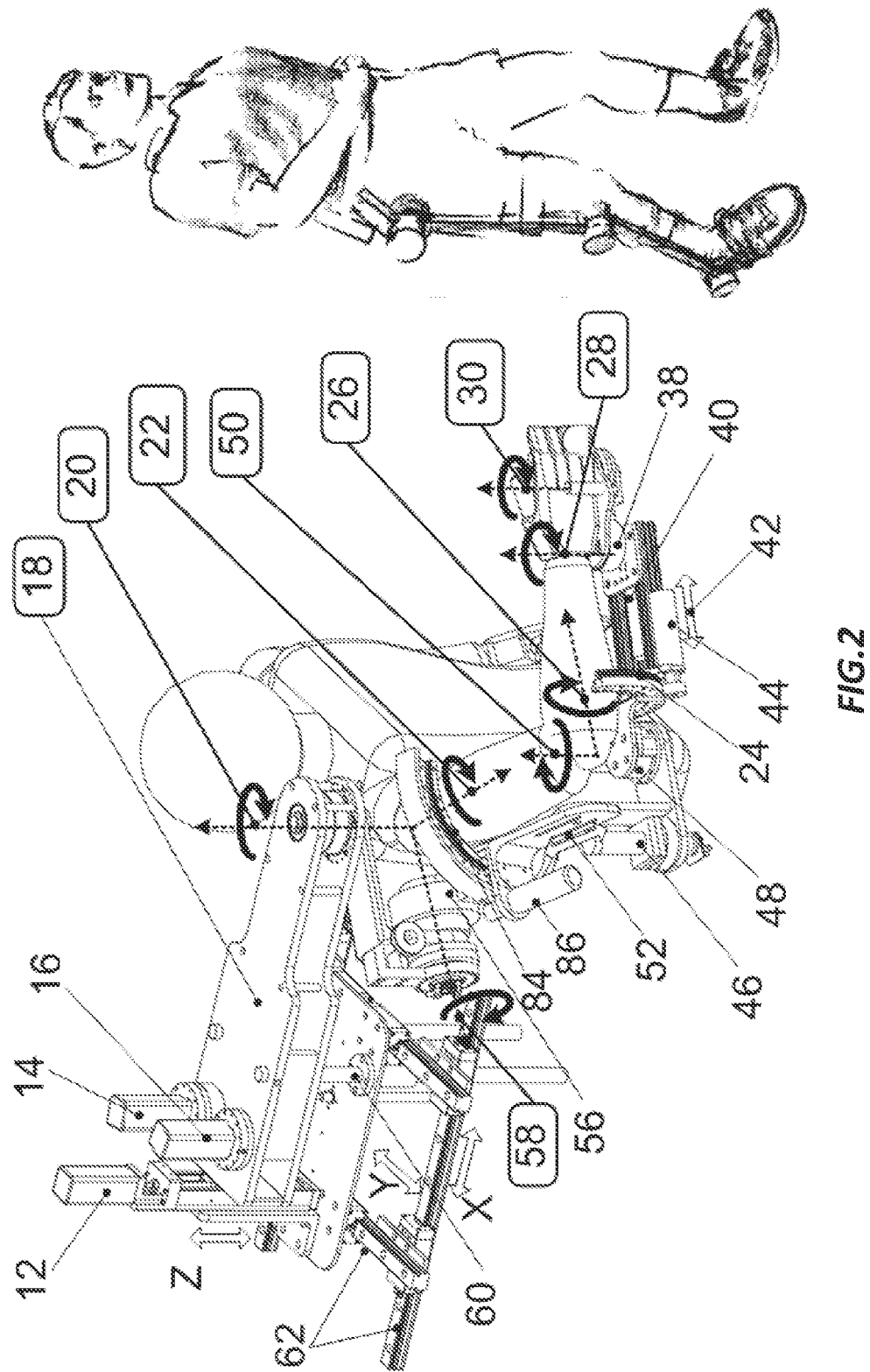
FIG. 2 shows the Robotic Apparatuses designed to diagnose, treat with both passive stretching and active functional movements, and evaluate multi-joint and multi-DOF biomechanical and neuromuscular changes in patients with limb impairments.

A.1 Robotic Apparatus Designed to Diagnose Multi-Joint/Multi-DOF Biomechanical Changes A custom-developed unique robotic apparatus is used to diagnose the biomechanical changes and abnormal couplings at the joints of the impaired limb of patients post stroke (FIG. 2).

For the upper limb, the shoulder, elbow and wrist are controlled in 8 active DOFs individually by 8 servomotors plus 2 passive DOFs, which is important in natural functional arm movements (FIG. 2a). For the lower limb, hip, knee and ankle are controlled in 3 active DOFs individually by 3 servomotors (FIG. 2b).

FIG. 2. The Robotic Apparatus designed to diagnose, treat with both passive stretching and active functional movements, and evaluate multi-joint and multi-DOF biomechanical changes including the upper limb (a) and lower limb (b).

Figure 3:
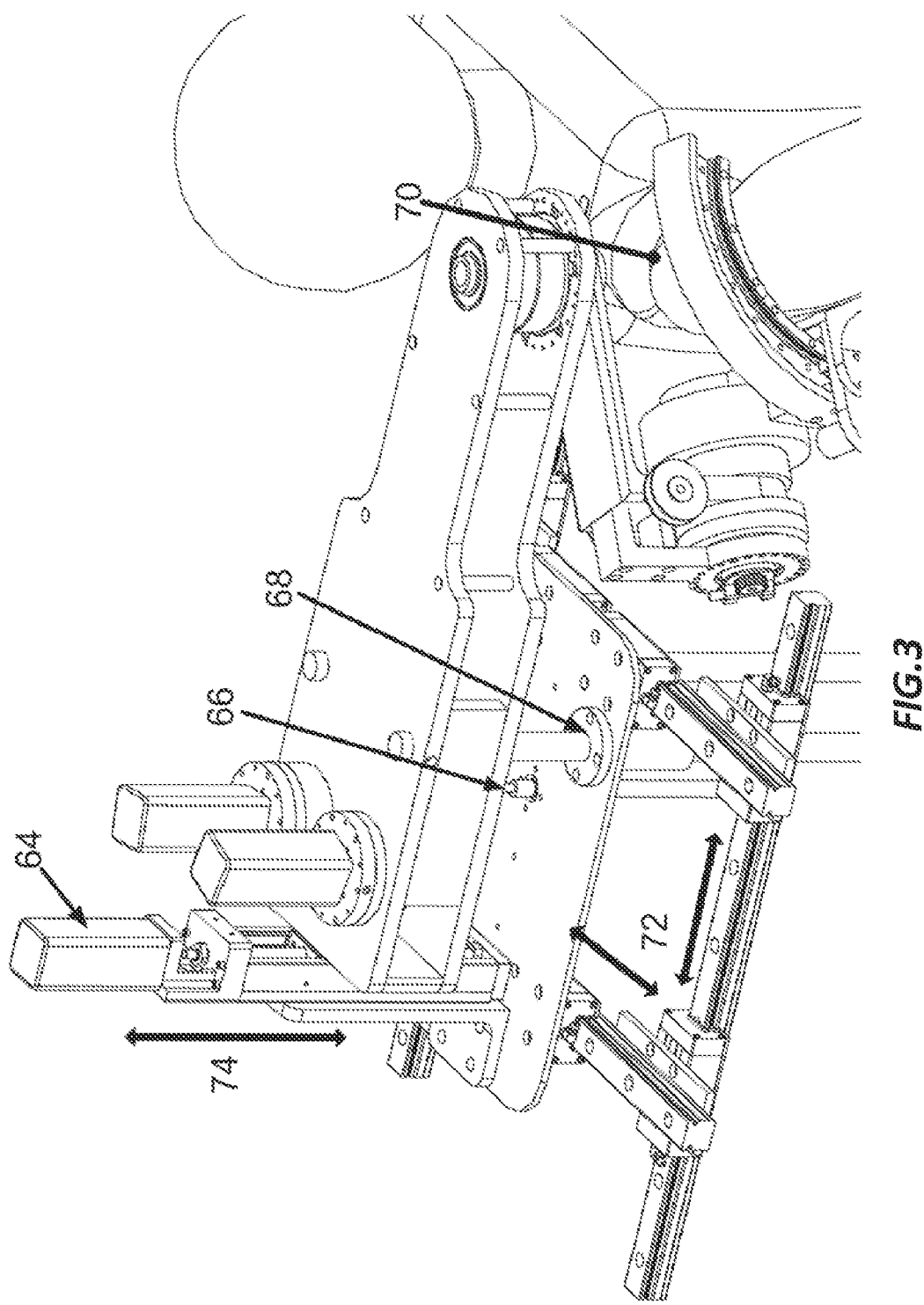
FIG. 3 is the mechanical design of the x-y-z motion.

For the upper limb, the robotic arm is mounted on an X-Y-Z table with the vertical Z-axis driven by a linear actuator and free to slide passively in the X-Y directions (FIG. 3). The whole device is mounted on the X-Y-Z table so that the glenohumeral joint can move in X-Y-Z directions to follow the scapular motion and trunk motion. Linear motion guides are used for the guiding in all three directions. Considering arm elevation involves both glenohumeral and scapular elevations and thus the glenohumeral joint moves in the vertical plane, the linear actuator controlling in the vertical direction and the free sliding in the mediolateral direction helps keep the robotic arm aligned with the glenohumeral joint. Furthermore, considering stroke survivors often use trunk leaning to compensate for their reaching motion, the robotic arm is free to slide in the anteroposterior direction to avoid unnatural restraints (FIG. 3). Weight supporting mechanism is used for reducing the size of the linear actuator because the mechanism supports most of the weight from the apparatus and the subject's limb.

Figure 4:
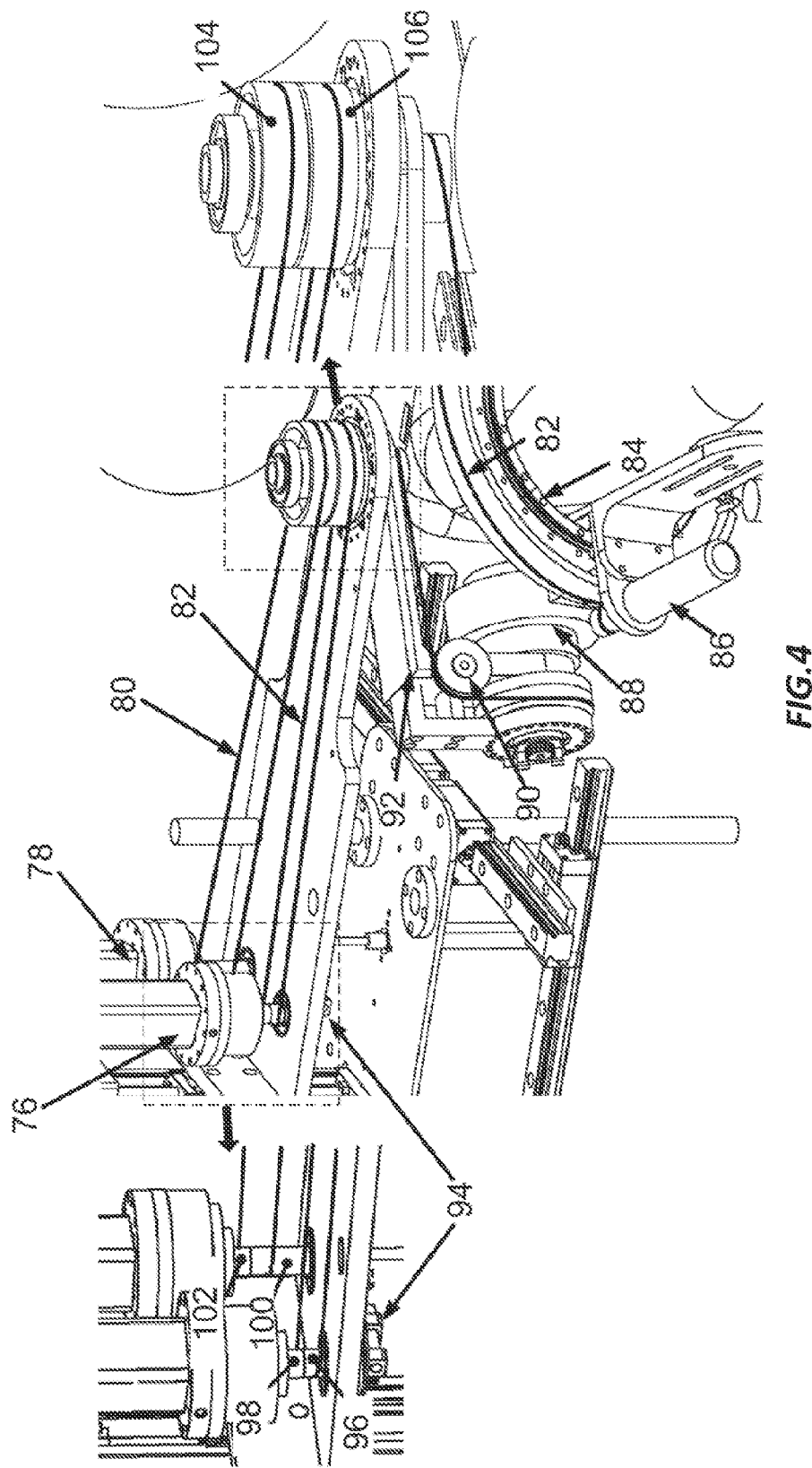
FIG. 4 is the mechanical design of the shoulder joint.

The glenohumeral joint is controlled actively in 3 DOFs: horizontal abduction/adduction, flexion/extension, and internal/external rotation (FIG. 4). Two motors for shoulder horizontal abduction/adduction and flexion/extension are located behind the subject and remotely drive the joint through cable mechanism. For the shoulder Horizontal Ab/Adduction, two cables are affixed to Shaft 1A and Shaft 1B wrapping in the opposite directions. The other ends of the two cables (dark red color) are affixed to Drum 1 with each cable wrapping in the opposite direction. The cables are tensioned tight using the cable tensioner composed of worm gear. Drum 1 is fixed to the shoulder horizontal link and moves the linkage. In the similar way, two cables (blue color) wrap around Shaft 2A and Shaft 2B to drive shoulder Flexion/Extension and the cables are affixed to Drum 2. From the bottom of Drum 2, another two cables drives the shoulder flexion/extension through pulleys to another two drums aligned with shoulder flexion/extension joint (yellow and green drums). The flexion/extension joint has two stages for the cable mechanism. Pulleys were used to change the direction of cable tension. The shoulder internal/external joint was driven by using circular guide on which the link is mounted. The motor travels around the joint with the link as the motor drives the joint through cable mechanism. A 6 DOF force/torque sensor is mounted between two links so that it measures the 3 forces (Fx, Fy, Fz) and 3 moments (Mx, My, Mz).

FIG. 3. Mechanical design for X-Y-Z motion.

FIG. 4. Mechanical Design of Shoulder Joint

Figure 5:
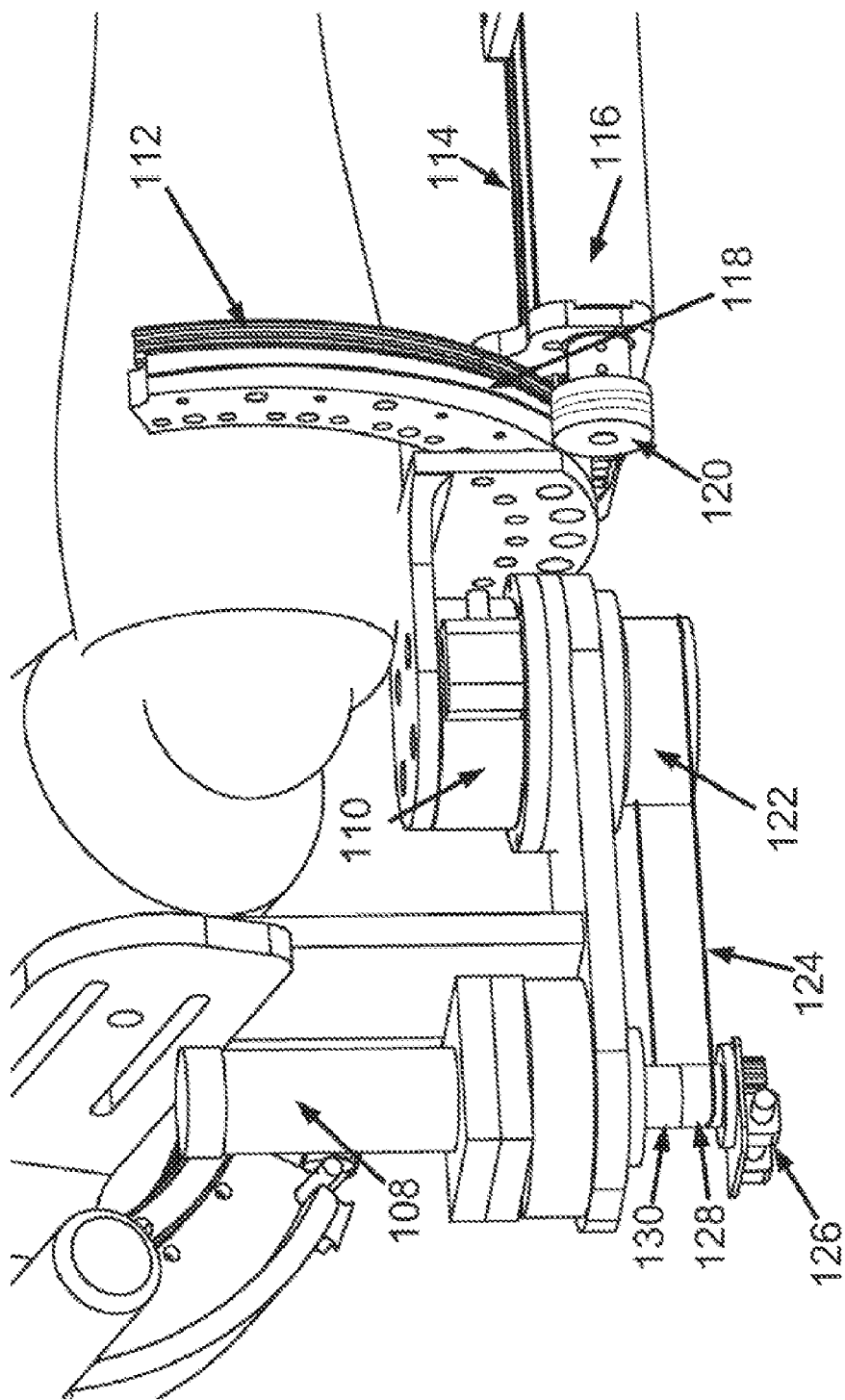
FIG. 5 is the mechanical design of the elbow joint.

At the elbow, the motor remotely drives the elbow flexion/extension joint through cable (FIG. 5) with the cable tensioner displayed in the figure. In this way, the motor driving the elbow joint can be placed along the linkage to save rooms under the robot. Without saving the rooms, the motor will take space under the robot and will hit the subject's body during the operation. Two cables wrap around Shaft 1A and Shaft 1B respectively and are fixed to Drum 1. Cable tensioner (worm gear) tightens the cables so that the elbow motor can drive the elbow joint without backlash. Patients post stroke often develop pronation deformity of the forearm, it is important to move and evaluate the forearm in a proper range of pronation. The forearm is mounted to a circular guide through a forearm brace (not shown in the figure for clarity) and controlled by a servomotor through a cable-driven mechanism, which allows controlled movement of forearm supination-pronation (FIG. 5). Two cables wrap around Drum 2 and are fixed to the two ends of the circular guide. As the motor rotates, the motor and the forearm links rotate around the circular guide creating motions for forearm supination and pronation.

FIG. 5. Mechanical design of the elbow joint.

Figure 6:
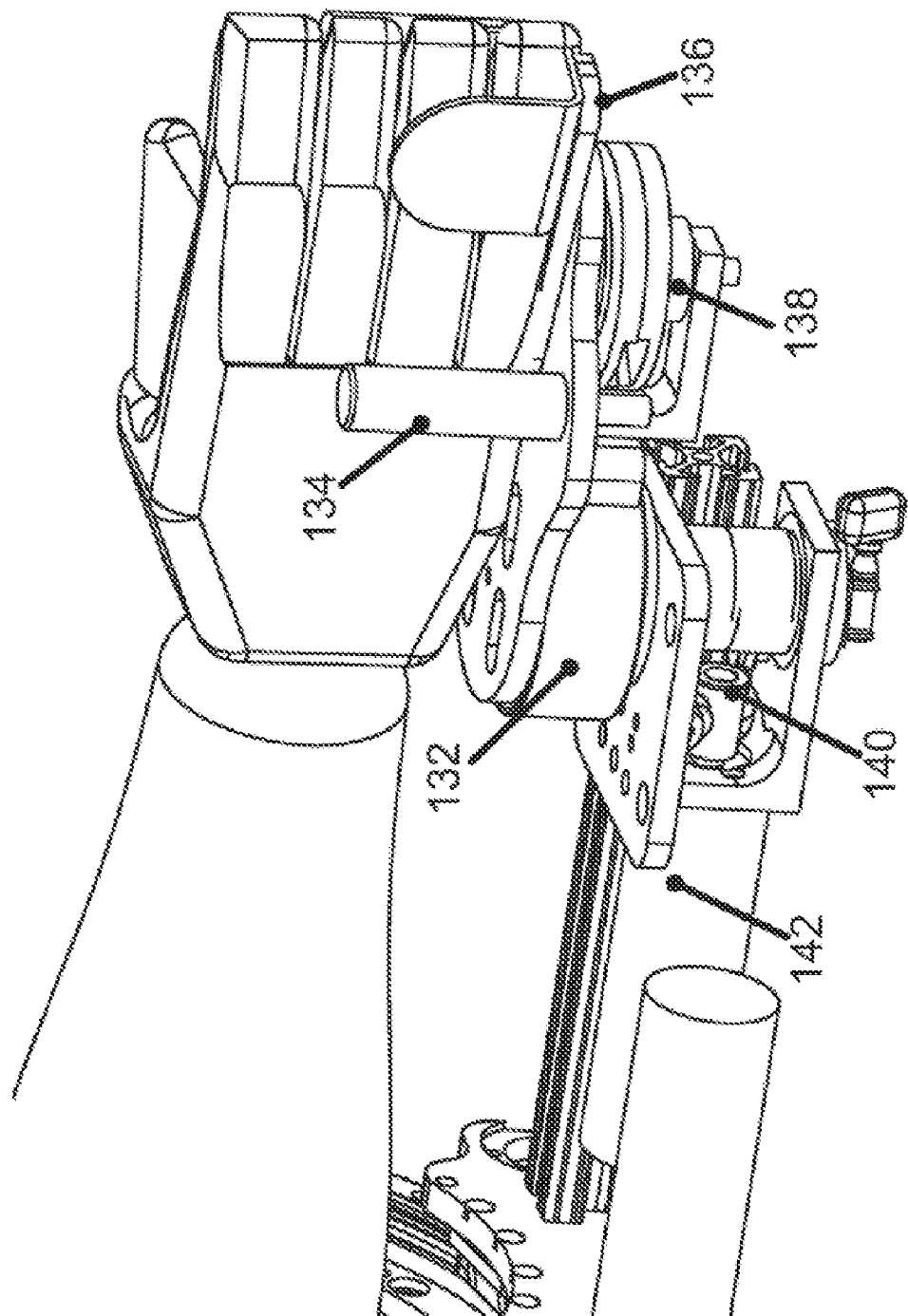
FIG. 6 is the mechanical design of the wrist and hand part.

The wrist is driven in flexion/extension by the wrist motor (FIG. 6). Wrist motor is located orthogonal to the wrist joint using bevel gear to save the rooms under the robot. A 6 DOF force/torque sensor measures forces and torques at the wrist joint. Patients post stroke often develop clinched fist and it is important to stretch their fingers to open the hand. Two-bar linkage driven by a motor selected for hand open/close while a torque sensor at MCP (metacarpophalangeal) joint measures the torques at the joint. Adjustable braces (not shown in the figure for clarity) hold the hand securely.

FIG. 6. Mechanical design of wrist and hand part.

To diagnose arm impairment in terms of multi-joint biomechanical properties, it is important to move the arm throughout its range of motion. In order to have anatomic range of motion at each joint, each joint in the robotic apparatus has the sufficient range of motion (Table 1). Direct driving of each joint/DOF at its axis using a servomotor provides large physiological ranges of motion at the shoulder, elbow, forearm and wrist (FIG. 2a), which is important in the multi-joint and multi-DOF diagnosis.

TABLE 1

Range of Motion of the robot

| Joint | ROM in ADL tasks | ROM (the robotic apparatus) |
|---|---|---|
| Shoulder H. Abd/Add | 120 deg | 135 deg |
| Shoulder Flex/Ext | 110 deg | 110 deg |
| Shoulder Int/Ext Rotation | 135 deg | 135 deg |
| Shoulder Vertical Displacement (due to scapular motion) | 150 mm | 200 mm |
| Elbow Flex/Ext | 120 deg | 130 deg |
| Forearm Supination/Pronation | 150 deg | 150 deg |
| Wrist Flexion/Extension | 115 deg | 150 deg |

Six-axis resistance torques/forces are measured at each of the joints including the shoulder, elbow and wrist (FIG. 2a). Each of the 8 DOFs plus the 2 passive DOFs is measured by encoders built in the servomotors or potentiometers mounted on the X-Y-Z table. The comprehensive kinetic and kinematic measurements allow us to evaluate the increased stiffness, abnormal couplings among the multiple joints and multi-DOFs, and loss of individuation to diagnose the pathological changes difficult to do in a manual examination by a clinician.

A.2 Diagnosis of Biomechanical Changes in the Impaired Arm

The subject sits upright comfortably on a sturdy barber's chair, with the trunk strapped to the backrest. The arm, forearm and hand are strapped to their corresponding braces, with the relevant axes of the apparatus aligned with the arm at the shoulder, elbow, and wrist (FIG. 2a). The position of the elbow and wrist servomotors can be adjusted along the arm and forearm for different arm and forearm lengths.

In diagnosing the multi-joint and multi-DOF biomechanical changes, the robotic apparatus operates in both passive and active modes. In the passive mode, the apparatus moves the joints of patients post stroke throughout the ROMs both simultaneously and individually in well-controlled patterns with the multi-axis torques and positions measured at all joints simultaneously. In the active mode, the patient moves the impaired limb voluntarily and the multi-joint and multi-DOF dynamic properties are measured at the all joints simultaneously.

Multi-joint and multi-DOF analysis is done on data from the Robotic apparatus to diagnose the multi-joint biomechanical changes in the impaired arm and evaluate the Robotic apparatus. For example, which joints and DOFs are coupled abnormally? What are the patterns of the abnormal coupling or coactivation? Which joints are stiff? Among the many possible measures, the ROM, stiffness at the shoulder, elbow and wrist, and coupling torques between the three joints are analyzed.

Loss of individuation can be evaluated through multi-joint and multi-DOF analysis. When a subject was asked to do horizontal adduction/abduction of the shoulder without moving the elbow and wrist, for example, a healthy subject could do that successfully (see the blue curve in FIG. 7a), while patients post stroke produced considerable coupled elbow flexion/extension movement. Furthermore, different patients could have different abnormal couplings. On the one hand, the patient with severe impairment (with the stereotypical pattern of adducted shoulder, flexed elbow, flexed wrist and clenched fist, and with control of the shoulder but not the elbow and wrist) showed coupled elbow flexion during shoulder horizontal abduction, indicating stiff elbow flexor muscles. On the other hand, the patient with mild impairment generated elbow extension during shoulder horizontal abduction, suggesting abnormal coactivation of the elbow extensor muscles during the shoulder horizontal abduction. The coupled elbow motion during shoulder horizontal adduction was confirmed by the corresponding elbow flexion torque in a similar task of shoulder horizontal adduction but with the elbow flexion fixed by the Robotic apparatus (FIG. 7b). Furthermore, during passive movement of the shoulder in horizontal adduction, similar coupling torque was generated in elbow flexion. However, the torque amplitude (~1.8 Nm, not shown here) was much lower than that in FIG. 7b (~14 Nm, the green line), indicating the abnormal coactivation of the elbow flexors (biceps and maybe others as well) during shoulder horizontal abduction was a more significant factor contributing to the coupled elbow torque/motion than the passive stiffness of the elbow flexors. Coactivation of the biceps was corroborated with EMG measurement (FIG. 8). Based on the diagnosis, the different patterns of abnormal couplings should be treated differently in the subsequent passive stretching and active movement therapy. For analysis abnormal coupling, the peak coupling torque is used.

Figure 7:
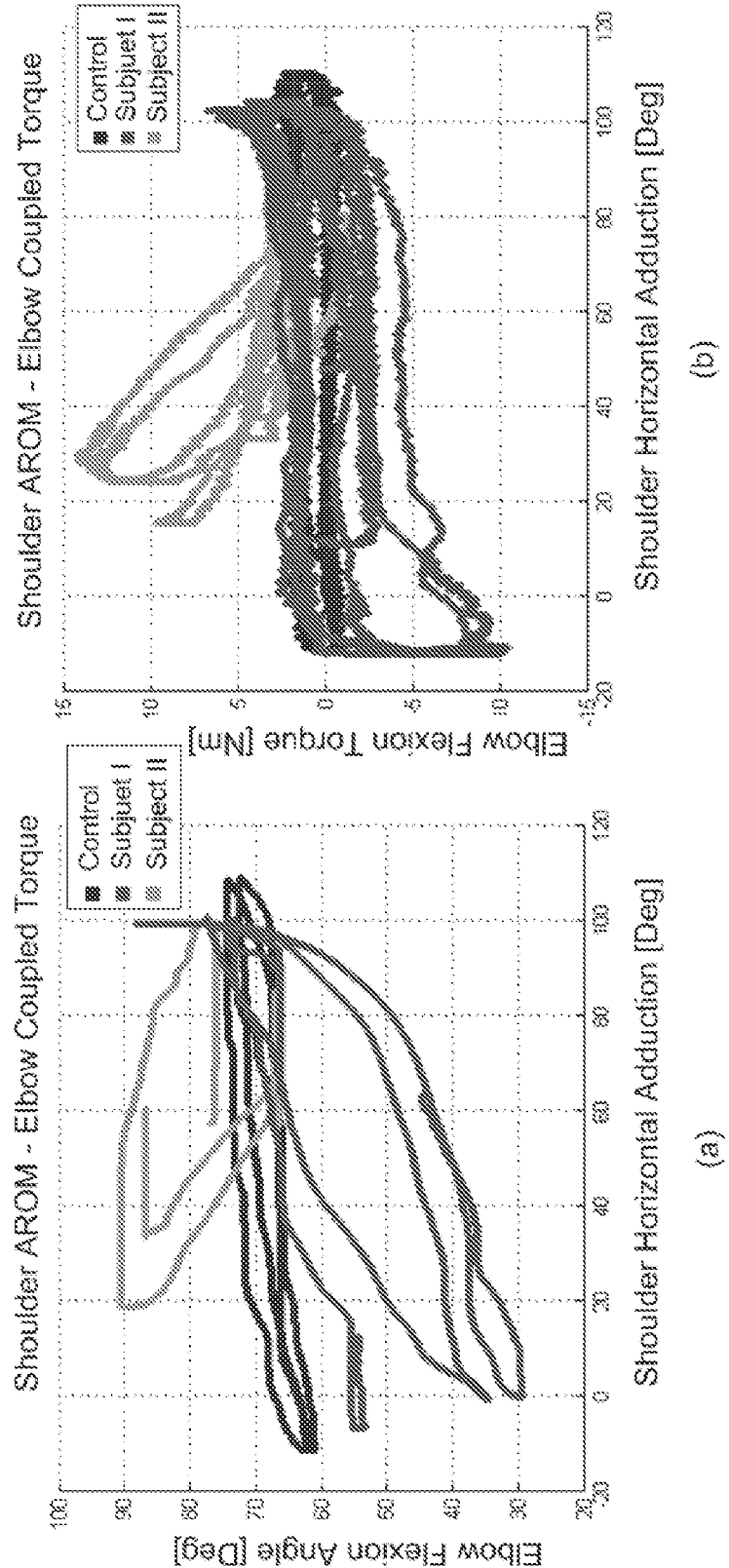
FIG. 7 is the graph presenting couplings between the shoulder and elbow, showing loss of independent control of an individual joint (called loss of individuation), with data collected using a 4-DOF arm rehabilitation robot. (a) Coupled elbow flexion/extension when the subject attempted to move his/her shoulder voluntarily in horizontal adduction. The subjects were asked to do horizontal adduction/abduction and the elbow and wrist were free to move. Marked elbow movement was seen in the patients post stroke, suggesting loss of individuation. Data were from a healthy subject (Control) and patients post stroke with mild (Subject I) and severe (Subject II) impairment. (b) A similar shoulder horizontal adduction task performed by the same three subjects but with the elbow and wrist held at their initial positions. Considerable coupling torque was seen at the elbow in the patients post stroke, in the directions consistent with the corresponding elbow joint movement in (a).
Figure 8:
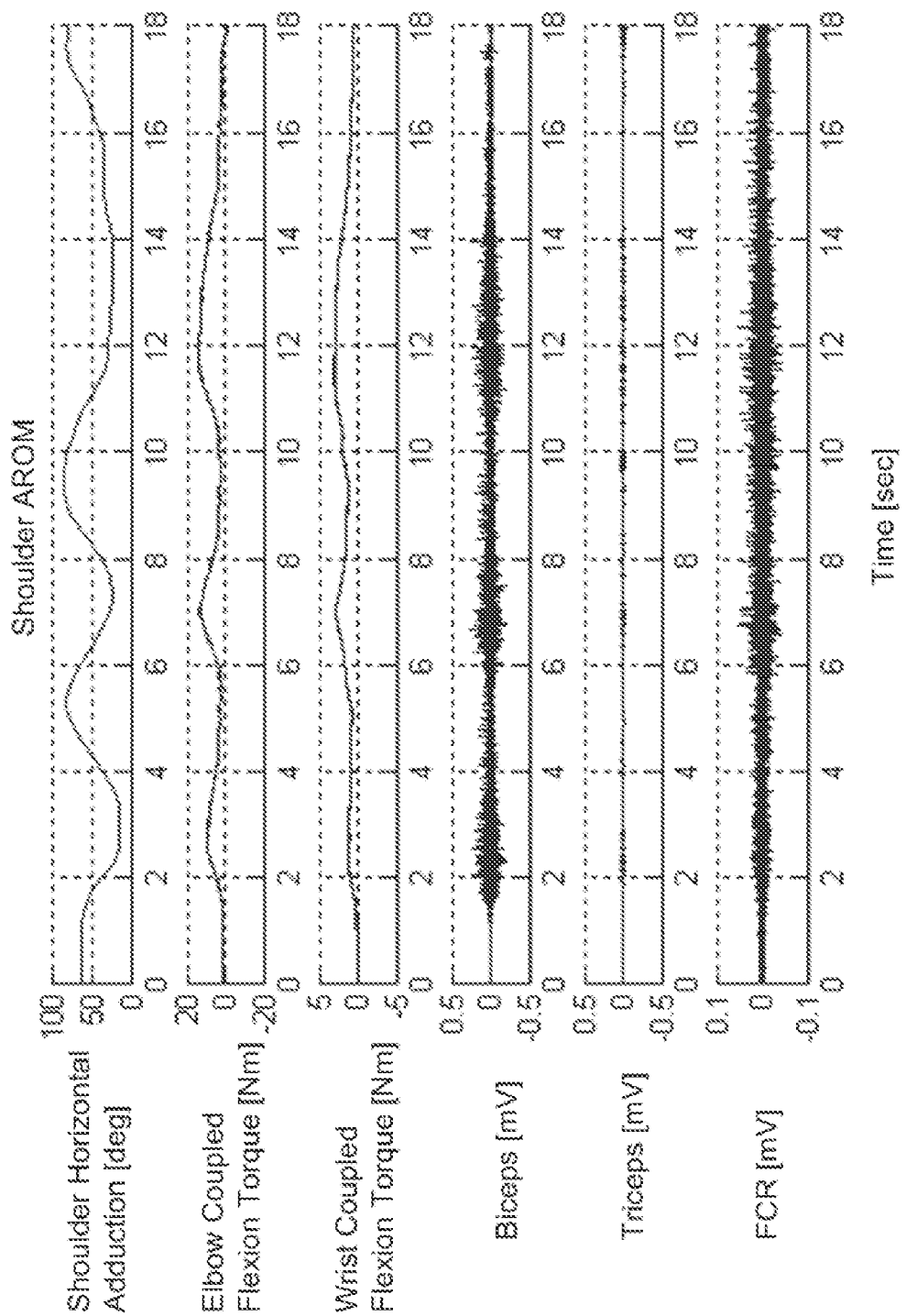
FIG. 8 is the graph showing biomechanical couplings between the shoulder and elbow and the loss of independent control of individual joints, with the data collected using a 4-DOF arm rehabilitation robot. EMG signals from selected muscles and cross-coupling torques at the elbow and wrist during the shoulder horizontal abduction movement task is shown in FIG. 3(b). Notice that the considerable coactivation of biceps and flexor carpi radialis (FCR, a wrist flexor in the forearm) muscles during the active shoulder horizontal abduction.

FIG. 7 Couplings between the shoulder and elbow, showing loss of individuation, with data collected with the 4-DOF arm rehab robot. (a) Coupled elbow flexion/extension when the subject attempted to move his/her shoulder voluntarily in horizontal adduction. The subjects were asked to do horizontal adduction/abduction and the elbow and wrist were free to move. Marked elbow movement was seen in the patients post stroke, suggesting loss of individuation. Data were from a healthy subject (Control) and patients post stroke with mild (Subject I) and severe (Subject II) impairment. (b) A similar shoulder horizontal adduction task performed by the same three subjects but with the elbow and wrist held at their initial positions. Considerable coupling torque was seen at the elbow in the patients post stroke, in the directions consistent with the corresponding elbow joint movement in (a).

FIG. 8. Couplings between the shoulder and elbow, showing loss of individuation, with data collected with the 4-DOF arm rehab robot. EMG signals from selected muscles and cross-coupling torques at the elbow and wrist during the shoulder horizontal abduction task shown in FIG. 7(b). Notice the considerable coactivation of biceps and FCR during the active shoulder horizontal abduction.

Figure 9:
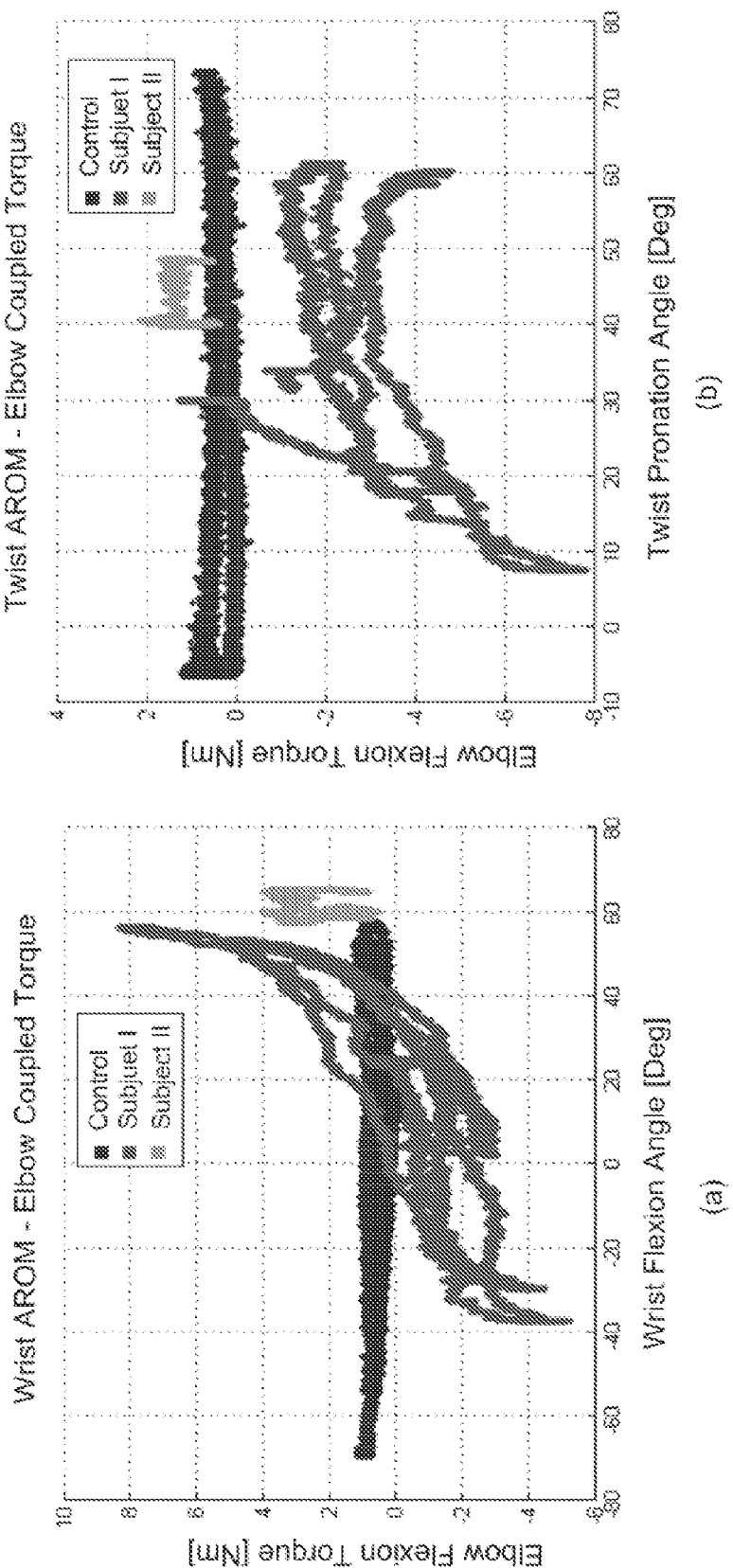
FIG. 9 shows the biomechanical couplings between the wrist and elbow flexion, with data collected with the 4-DOF arm rehab robot. (a) Couplings between the wrist and elbow flexion, with data collected with the 4-DOF arm rehab robot. The subject was asked to flex and extend the wrist throughout its ROM with the other joints held at the initial position. Data were from a healthy subject (Control) and patients post stroke with mild (Subject I) and severe (Subject II) impairment. Notice that the patient with severe impairment (Subject II) could not move her wrist. (b) Coupled elbow flexion torque when the subjects attempted to twist his/her forearm voluntarily. The subject was asked to supinate and pronate the forearm throughout its ROM with the other joints held at the initial position. Substantial coupling torque was seen at the elbow flexion axis. Data were from a healthy subject (Control) and patients post stroke with mild (Subject I) and severe (Subject II) impairment.

Abnormal couplings can be similarly analyzed for the distal joints. For example, when the subjects were asked to flex/extension the wrist isolately without moving other joints, the healthy subject (Control) could do so successfully, while the patient with mild impairment generated substantial elbow flexion torque (Subject I) and the patient with severe impairment (Subject II) could not move the wrist and generated some torque at the elbow through its coupling with the shoulder (FIG. 9a). Similarly, when the subjects were asked to supinate/pronate the forearm with moving in other joints, the healthy subject could do it successfully. The patient with mild impairment showed substantial coupling torque about the elbow flexion axis (Subject I) while the patient with sever impairment could not control the forearm twisting (Subject II) (FIG. 9b).

FIG. 9(a) Couplings between the wrist and elbow flexion, with data collected with the 4-DOF arm rehab robot. The subject was asked to flex and extend the wrist throughout its ROM with the other joints held at the initial position. Data were from a healthy subject (Control) and patients post stroke with mild (Subject I) and severe (Subject II) impairment. Notice that the patient with severe impairment (Subject II) could not move her wrist. (b) Coupled elbow flexion torque when the subjects attempted to twist his/her forearm voluntarily. The subject was asked to supinate and pronate the forearm throughout its ROM with the other joints held at the initial position. Substantial coupling torque was seen at the elbow flexion axis. Data were from a healthy subject (Control) and patients post stroke with mild (Subject I) and severe (Subject II) impairment.

Figure 10:
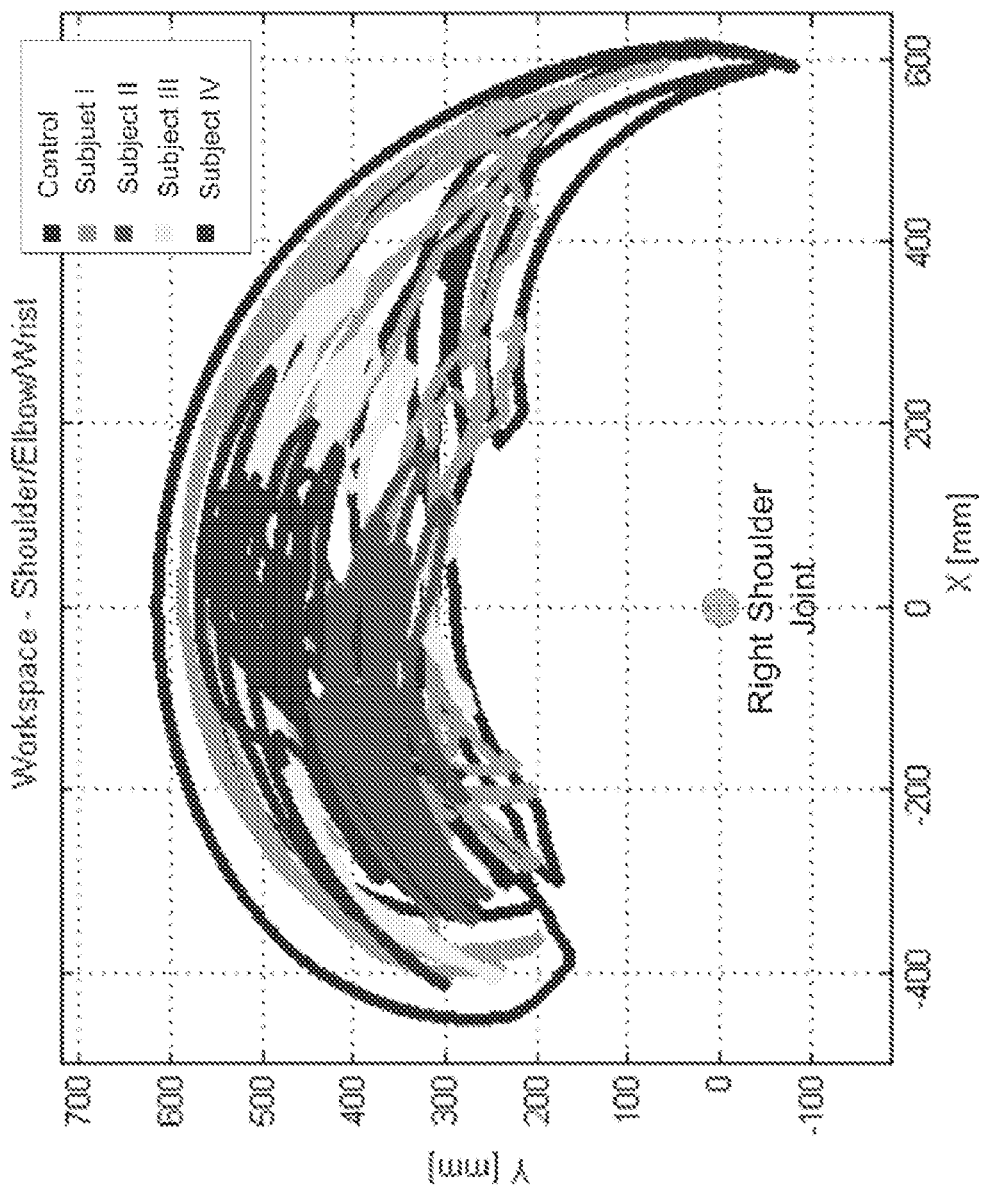
FIG. 10 is the active workspace of voluntary reaching movement in the horizontal plane and in the corresponding joint space, with data collected with the 4-DOF arm rehab robot. Data were from a healthy subject (Control) and 4 patients post stroke with various degrees of impairment. The focus of the testing was on the reaching and arm extension directions instead of the flexed positions.
Figure 11:
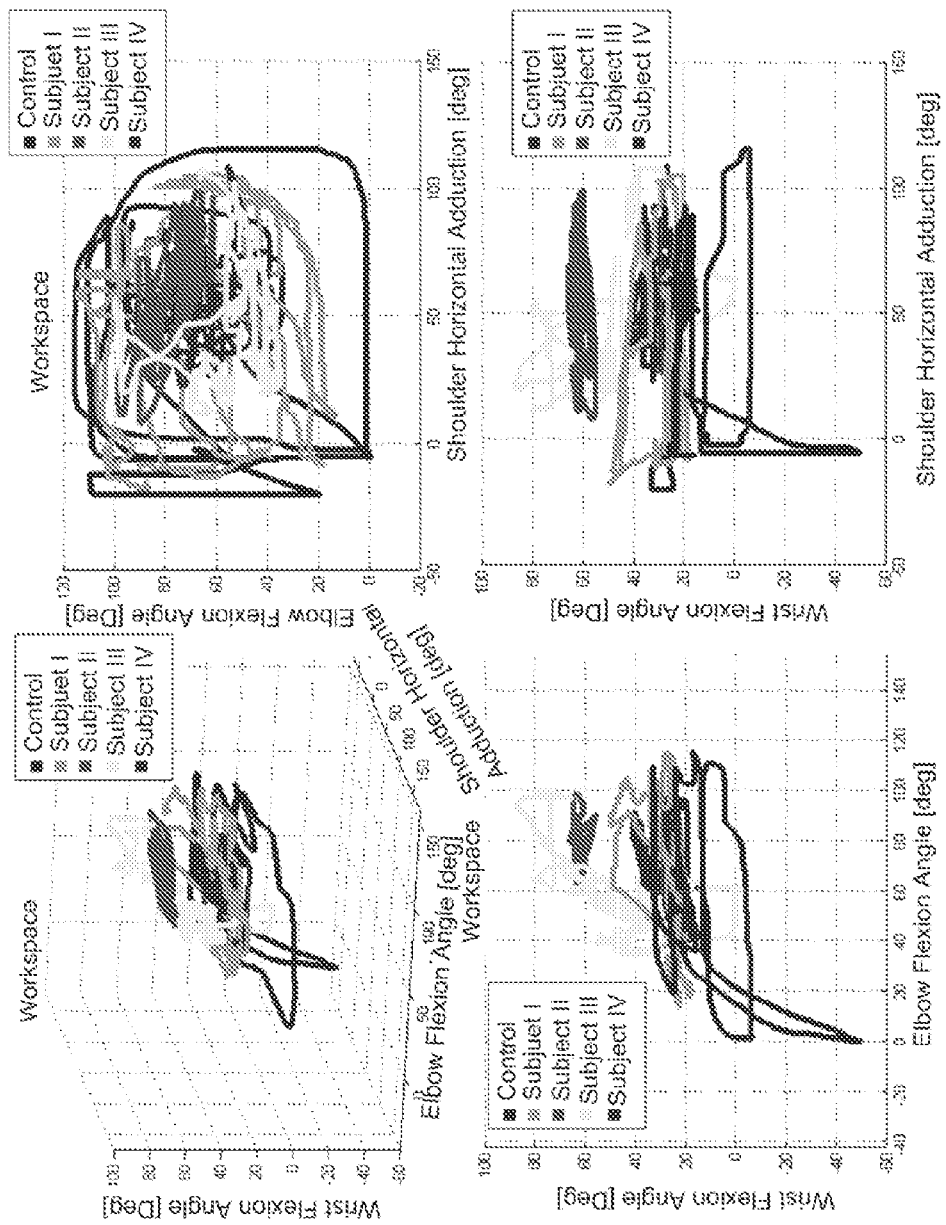
FIG. 11 is the active workspace of reaching in the joint space, with data collected with the 4-DOF arm rehabilitation robot. Data were from a healthy subject (Control) and 4 patients post stroke with various degrees of impairment. The focus of the testing was on the reaching and arm extension directions instead of the flexed positions.

The limited reaching workspace shown by the patients post stroke (FIG. 10) can be analyzed further at the level of individual joints (FIG. 11) for better understanding of the reduced workspace and potentially guiding therapy. As shown, patients with different degrees of impairment showed different amount of workspace reduction (FIG. 10 and FIG. 11). The reduced workspace for different patients may be due to different changes at the individual joint level, some may be more due to restricted wrist movement and some may be due to combination of the elbow and wrist (FIG. 11). In the 3-D joint space (top-left plot in FIG. 11), the patients had hard time to reach the extended positions. The subject's reaching data are analyzed to determine the specific joints contributing to the reduced workspace. Similar analysis is done for the workspace during passive movement driven by the Robotic apparatus.

FIG. 10. Active workspace of reaching in the horizontal plane and at the corresponding joint space (see FIG. 11 below), with data collected with the 4-DOF arm rehab robot. Data were from a healthy subject (Control) and 4 patients post stroke with various degrees of impairment. The focus of the testing was on the reaching and arm extension directions instead of the flexed positions.

FIG. 11. Active workspace of reaching in the joint space, with data collected with the 4-DOF arm rehab robot. Data were from a healthy subject (Control) and 4 patients post stroke with various degrees of impairment. The focus of the testing was on the reaching and arm extension directions instead of the flexed positions.

B. Passive Stretching of all Joints of the Impaired Limb Strenuously and Safely Under Intelligent Control Based on the Above Diagnosis to Reduce Hypertonia and Abnormal Coupling at the Joints Involved.

From the robotic diagnosis, the joints (and DOFs) with excessive coupling and/or increased stiffness and the associated limb postures are identified, the robotic apparatus stretches all the joints simultaneously in general between the curled (flexed) limb positions and extended limb positions. We also focus more on the joints/DOFs which need to be loosened up based on the above individual diagnosis. The robotic apparatus is under novel multi-joint intelligent control to stretch the joints forcefully and safely in well-coordinately patterns. On the one hand, for safe treatment, the stretching velocities decreases with increasing resistance torques at the multiple joints involved and each joint is stretched according to its own condition and the conditions of the coupled joints. On the other hand, for effective treatment, the stretching does not stop until pre-specified peak resistance torques are reached at the joints involved (and at individual DOFs). The stretched limb is held at the extreme positions for a period of time to let stress relaxation occur before the joints are moved to other extreme positions.

B.1 Stretch Multiple Joints/Multi-DOFs Under Intelligent Control

The joints in the impaired limb with deformity/hypertonia in patients post stroke are stretched forcefully and safely under intelligent control to loosen up the stiff muscles and joints (FIG. 2). The subject is seated upright comfortably on a barber chair, with the trunk strapped to the backrest. The segments in limbs are strapped to the apparatus through braces, respectively. Mechanical clamps are used to fix any of the braces to the robotic apparatus more securely.

The robotic apparatus is driven by multiple servomotors controlled by a digital controller, which can either drive all or several the joints/DOFs simultaneously or drive a joint individually. Based on the diagnosis, we know which joints are stiff, coupled abnormally, and need to be loosened up. For each servo system, the digital controller reads the joint position and resisting torques and adjusts the stretching velocity accordingly.

Based on a novel intelligent stretching strategy, the digital controller controls the stretching velocity at each joint according to the resistance torque as follows. Near the end of ROM, the increasing resistance slows down the motor gradually, which is critical for safe operation. Furthermore, the stretching does not stop until a pre-specified peak resistance torque is reached. In this way, the muscle-tendons involved are stretched strenuously and safely, which likely results in a larger ROM. Once the specified peak resistance torque is reached, the servomotor holds the joint at the extreme position for a period of time (e.g., 5 sec during each cycle of the back-and-forth stretching), as used by a therapist. In the middle ROM where the resistance is usually low, the motor stretches the slack muscles quickly at higher speeds. As a safety precaution, position limits can be set by the operator and they are monitored by the digital controller together with the torque limits. Specifically, the following rules are implemented in the digital controller to adjust the motor velocity $V(t)$ every 0.5 msec:

$$V(t) = \begin{cases} 0, & \text{if } (M_{res}(t) \geq M_p \text{ or } \theta(t) \geq \theta_p + \theta_d) \\ & \text{and need to hold} \\ -V_{max}, & \text{if } (M_{res}(t) \geq M_p \text{ or } \theta(t) \geq \theta_p + \theta_d) \\ & \text{and have held long enough} \\ \max\left(\dfrac{C}{M_{res}(t)}, V_{min}\right), & \text{if } 0 < M_{res}(t) < M_p \\ \min\left(\dfrac{C}{M_{res}(t)}, -V_{min}\right), & \text{if } -M_p < M_{res}(t) < 0 \\ V_{max}, & \text{if } (M_{res}(t) \leq -M_n \text{ or } \theta(t) \leq \theta_n - \theta_d) \\ & \text{and have held long enough} \\ 0, & \text{if } (M_{res}(t) \leq -M_n \text{ or } \theta(t) \leq \theta_n - \theta_d) \\ & \text{and need to hold} \end{cases} \quad (1)$$

where $\theta(t)$ and $M_{res}(t)$ are the joint position and resistance torque at time t, respectively. $M_p$ and $M_n$ are the specified peak resistance torque at the positive and negative ends of the joint ROM, respectively (both are positive numbers). $V_{min}$ and $V_{max}$ (positive numbers) are the magnitudes of the lowest (for stretching in the joint extreme positions) and highest speed (for stretching in the mid-ROM), respectively. C is a constant, scaling the $1/M_{res}(t)$ to the appropriate stretching velocity. $\theta_p$ and $\theta_n$ are the specified positive and negative end of the ROM, respectively. $\theta_d$ (a non-negative number) represents the allowed further rotation beyond the position limits (to leave room for stretching-induced improvement in ROM). If $\theta_d$ is chosen to be a very large number (to allow the device move beyond the position limits) or if $\theta_p$ and $\theta n$ are set outside the ROM, the stretching control is dominated by the resistance torque (the stretching is still safe) and the motor reverses its rotation once the specific resistance torque is reached for the specified amount of time. On the other hand, if $M_p$ and $M_n$ are chose to be very large, the stretching is restricted by the position limits. In general, we want the stretching reaches the torque limits at both ends of the ROM with the position limits incorporated into the control scheme as a safety measure and as an optional mode of stretching, therefore the $\theta_p$ and $\theta_n$ are set to approximately match the ROM by manually pushing the joint to its extreme positions (or by entering their values through the keyboard) and the $\theta_d$ is chosen as a positive number (e.g., 5°). In this way, the torque limits are reached most of the time, while the position limits still restrict potential excessive joint movement. All the control parameters can be adjusted conveniently within pre-specified ranges.

The digital controller checks the joint position and torque signals 2000 times per second and will shutdown the system if they are out of pre-specified ranges. Mechanical and electrical stops can be used to restrict the motor range of motion. The operator and the patient each have a stop switch, and either of them can shut down the apparatus by pressing the switch.

B.2 Control of Multiple Joints Coordinately

Considering that there are dozens of muscles and other soft tissues crossing the shoulder, elbow, and wrist joints or hip, knee, and ankle joints and some crossing two joints, movement and control of the joints are closely coupled. Furthermore, the couplings may be increased considerably in hypertonic and deformed limbs of patients post stroke. For more effective treatment of hypertonic limb, all the joints should be treated together in a well-coordinated way. Considering the limb deformity is characterized with adducted and internally rotated shoulder, flexed elbow and wrist and pronated forearm, and hypertonia may exist in both extension and flexion ends of the joints, the shoulder, elbow, and wrist joints are stretched simultaneously by the apparatus between overall whole arm stretched out and curled in positions.

There are infinite numbers of possible control modes during the stretching. In the 7-D joint space with 7-DOF active control at the shoulder, elbow and wrist, there are infinite number of paths between the whole arm curled position to the whole arm stretched position. The specific control mode or hand path is dependent on the ROMs and stretching speed at the shoulder, elbow, and wrist. The multiple joints and DOFs are stretched following the several rules:

Start with a neutral position with shoulder at 60° abduction and 30° flexion, elbow at 60° flexion, wrist at 25° flexion, and forearm at the 60° supination. If the patient's arm can not be put at the posture comfortably, the closest position is used.

Stretch the shoulder into abduction/extension/external rotation, elbow and wrist into extension, and forearm into supination simultaneously under intelligent control with specified the peak resistance torques and with the stretching velocity decreased with increasing resistance, as described above for individual joints/DOFs (Eq. (1)).

When one joint or DOF reaches the extreme extended/abducted/externally rotated/supinated position, hold it at the extreme position and wait for the other joints/DOFs to reach their extreme positions as well. As these other joints are being stretched to reach their peak resistance torque (or position) limit, the resistance torque at the first joint(s) which already reaches the torque limit may go beyond the torque limit due to coupling between the joints/DOFs. If the extra torque beyond the specified limit is within a pre-specified range (e.g., 1.5 Nm), the first joint(s) is kept at the held position. Otherwise, the first joint(s) is moved back a bit until the resistance torque is back at the torque limit.

Once all the joints/DOFs reach the extreme extension/supination, hold the arm at the posture for a period of time (e.g., 5 seconds) to let stress relaxation occur and the stiff joints become more compliant.

The arm is moved back towards the initial neutral position and it is held there for a period of time (e.g., 1 sec.), which provides us a measure of arm biomechanical properties at the common position in the stretching process.

Next, the arm is stretched towards the whole arm curled (adducted, internally rotated, flexed and pronated) extreme position. The stretching is controlled similarly as in the case of stretching into extended/abducted/externally rotated/supinated extreme positions.

The back and forth stretching process is repeated until a pre-specified stretching period (e.g., 10 minutes) is reached or a stop switch is pushed.

The operator may adjust the stretching limits and stretch at more strenuous levels.

For pilot data, stretching has been done successfully under intelligent control on patients post stroke with arm hypertonia and stereotypical deformity. Simultaneous shoulder, elbow and wrist stretching is used as treatment to loosen up the stiff muscles-joints of the arms with hypertonia/deformity, while isolated shoulder, elbow or wrist passive movement is used to evaluate the multi-joint dynamics including couplings among the joints.

Figure 12:
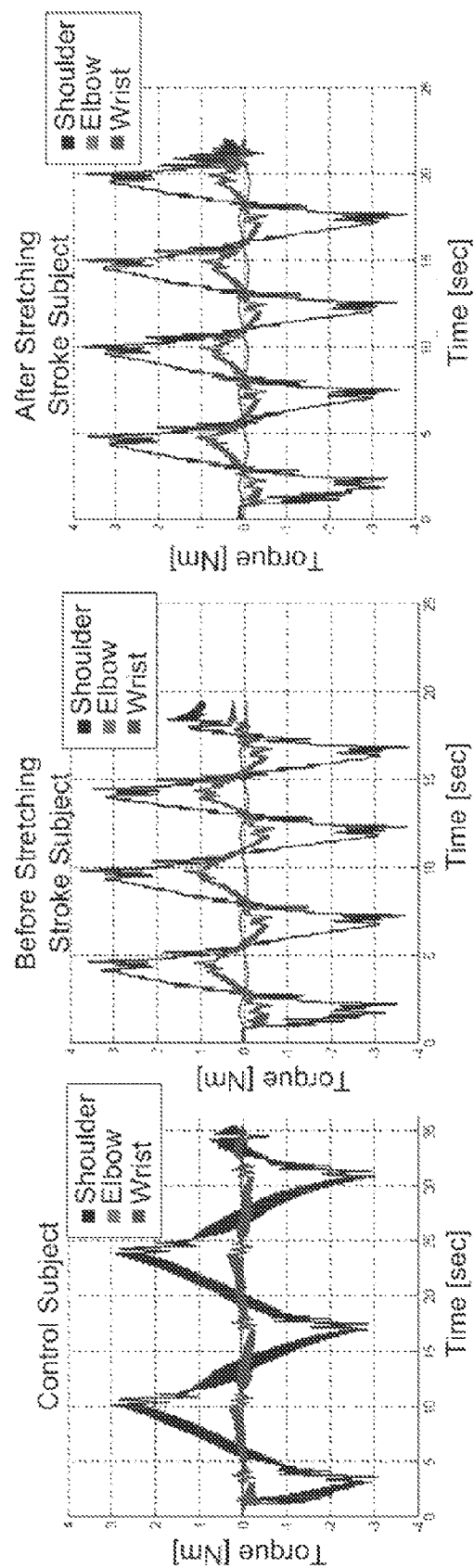
FIG. 12. is the data collected during stretching while the shoulder was stretched during horizontal abduction movement at a relatively low level of peak resistance torque (about ±3 Nm). Joint torques at the shoulder, elbow and wrist during the shoulder stretching from a healthy subject (a) and a patient post stroke with considerable arm hypertonia/deformity (b and c) are shown. For the patient, joint torques from similar stretching trials at the beginning and end of the stretching session are shown in (b) and (c), respectively.

When the shoulder is stretched back and forth in horizontal abduction with the elbow and wrist held at constant positions, there is a considerable flexion toque generated at the elbow and wrist, following roughly the pattern of the shoulder torque, probably related to the stiff arm muscles crossing the joints (FIG. 12). Compared with healthy subject, the hypertonic arm of the patient post stroke produced several fold higher coupling torques at the elbow and wrist joints (FIG. 12). Furthermore, after strenuous stretching of shoulder, elbow and wrist joints simultaneously for about 30 min, the coupling torques at the elbow and wrist when the shoulder is stretched are reduced considerably (FIGS. 12b and c).

FIG. 12. The shoulder was stretched in horizontal abduction at low torque level (about ±3 Nm) using the 4-DOF arm rehab robot. Joint torques at the shoulder, elbow and wrist during the shoulder stretching from a healthy subject (a) and a patient post stroke with considerable arm hypertonia/deformity (b and c) are shown. For the patient, joint torques from similar stretching trials at the beginning and end of the stretching session are shown in (b) and (c), respectively.

Stretching-induced improvement can be analyzed and shown clearly in 3-D joint space, with the shoulder, elbow and wrist stretched simultaneously (FIG. 13a). For further detail during the stretching including the stretching-induced improvement, the kinematic and kinetic data can also be shown together as function of time (FIG. 13b). The Robotic apparatus stretched arms with hypertonia/deformity strenuously and safely, and patients post stroke like the stretching and feel it loosen their stiff arms. Some relevant analysis results are given here. For examples, paired t-test showed that both the elbow extension (P=0.01) and flexion (P=0.03) ROMs measured at controlled resistance were improved significantly after the strenuous stretching. With the same subjects, wrist extension also increased significantly with P=0.002 (paired t-test). Wrist flexion did not change considering that the wrists were hypertonic and deformed in flexion.

The strenuous and yet safe stretching loosen the stiff joints and make them significantly less stiff. At comparable joint positions, both elbow extension (P=0.005) and flexion (P=0.042) stiffness are reduced after a session of strenuous stretching. Wrist joint stiffness is also reduced significantly in both extension (P=0.024) and flexion (P=0.044) (paired t-test).

Figure 13:
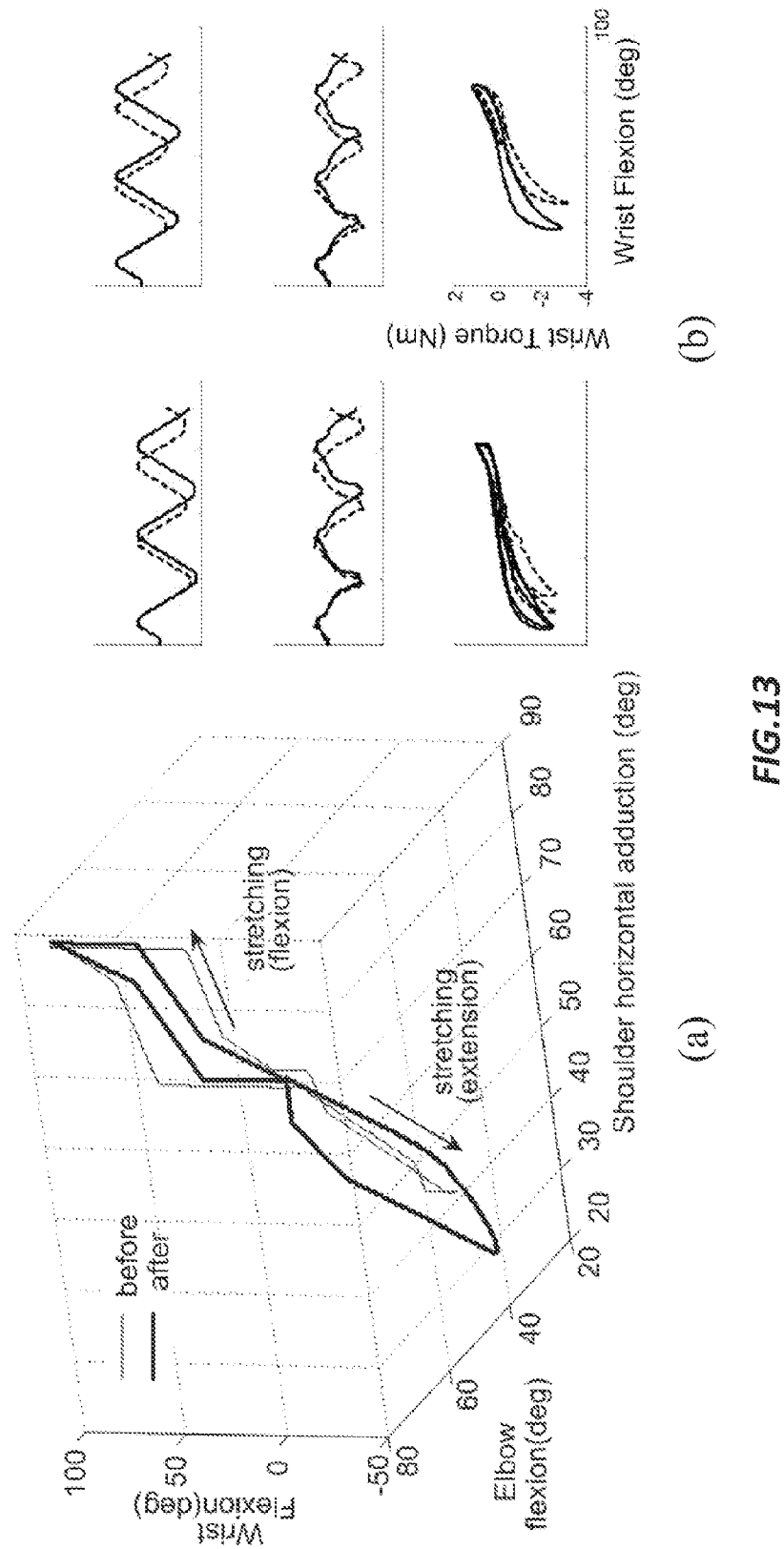
FIG. 13 shows the shoulder, elbow and wrist passive ROMs (passive workspace) from a patient post stroke with considerable arm hypertonia/deformity. (a) The shoulder, elbow and wrist passive ROMs (passive workspace) from a patient post stroke with considerable arm hypertonia/deformity, determined using the 4-DOF arm rehab robot and shown in 3-D joint space. (b) Stretching data from a stroke patient with substantial hypertonia/deformity at the elbow and wrist. The elbow and wrist of a stroke patient with arm deformity and hypertonia were stretched simultaneously using the Robotic apparatus. The left and right columns correspond to data the elbow and wrist, respectively. The 1st and 2nd rows show the elbow and wrist flexion angles and elbow and wrist flexion torque (elbow and wrist flexor resistance torque was negative) as functions of time. The 3rd row shows the torque-angle curve at the two joints and the slope of the curves corresponds to the joint stiffness. The blue dashed line and red solid line correspond to data at the beginning and end of a stretching session, respectively.

FIG. 13. (a) The shoulder, elbow and wrist passive ROMs (passive workspace) from a patient post stroke with considerable arm hypertonia/deformity, determined using the 4-DOF arm rehab robot and shown in 3-D joint space. (b) Stretching data from a stroke patient with substantial hypertonia/deformity at the elbow and wrist. The elbow and wrist of a stroke patient with arm deformity and hypertonia were stretched simultaneously using the Robotic apparatus. The left and right columns correspond to data from the elbow and wrist, respectively. The $1^{st}$ and $2^{nd}$ rows show the elbow and wrist flexion angles and elbow and wrist flexion torque (elbow and wrist flexor resistance torque was negative) as functions of time. The 3rd row shows the torque-angle curve at the two joints and the slope of the curves corresponds to the joint stiffness. The blue dashed line and red solid line correspond to data at the beginning and end of a stretching session, respectively.

Figure 14:
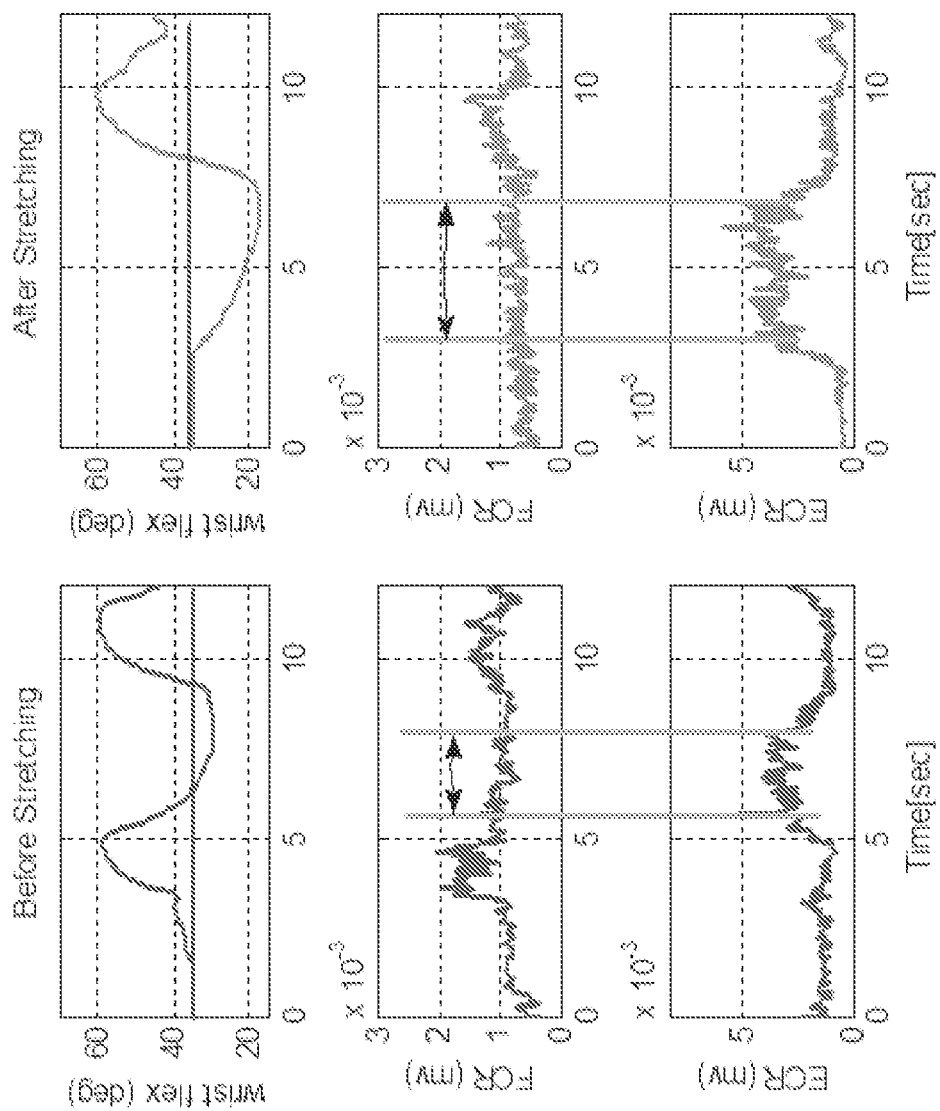
FIG. 14 is the experimental data during voluntary wrist extension before (left column) and after (right column) the stretching treatment with reduced flexor-extensor co-contraction.

With the strenuous stretching loosening up the stiff joints, the CNS may be able to control the muscles and move the joint more properly. During the active wrist extension, a patient with difficulty extending the wrist voluntarily (left column of FIG. 14) could control it more easily and moved it further into wrist extension after stretching (right column of FIG. 14). The improvement may be due to reduced co-contraction of wrist flexors as well as improved control of the wrist extensors. The flexor/extensor co-contraction ratio during the extension task was reduced from 29.6% to 20.0% (FIG. 14). Wrist extension MVC of the subject was similarly improved, partly due to the reduction in co-contraction.

FIG. 14. Voluntary wrist extension before (left column) and after (right column) stretching with reduced flexor-extensor cocontraction.

C. Voluntary Movement Training after the Passive Stretching Loosens the Stiff Muscles.

Motor impairment is associated with both neural and peripheral biomechanical changes. After the intelligent stretching reduces the abnormal joint coupling and stiffness, the neural command may be able to better control the muscles and move the arm. The robotic apparatus is controlled backdrivable so that patients can move the limb with the apparatus freely to match or track targets displayed on a computer screen during the movement training. The movement training is done in the form of computer games to motivate the patients and enhance the motor relearning (FIG. 15).

Figure 15:
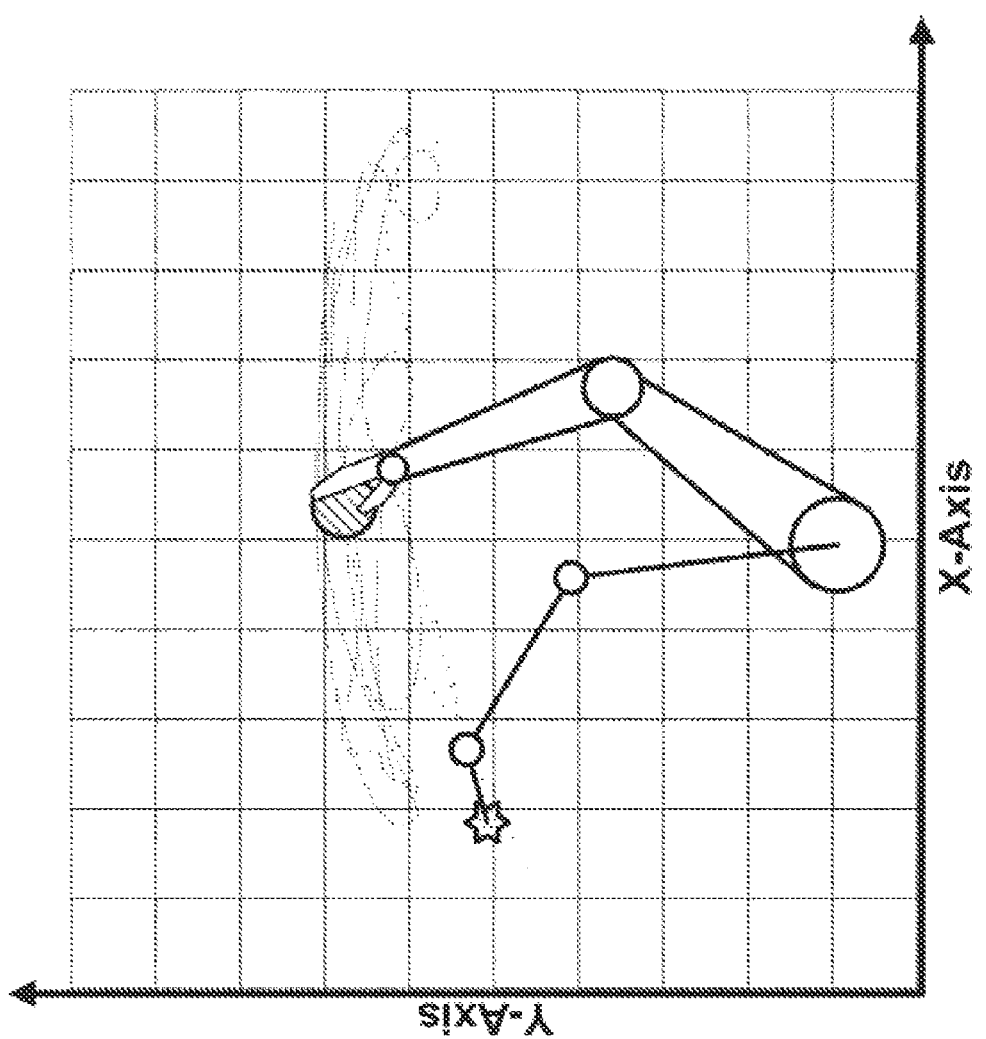
FIG. 15 is the screen shot of the hand reaching exercise software designed to improve voluntary movement control. The hand reaching exercise designed to improve voluntary motor control. The shoulder, elbow and wrist angles are displayed in real-time (represented by the three circles). The subject is asked to move the hand from the current position (the circle with hashed lines) to the target (the star) by placing the circle around the star, while keeping the shoulder, elbow and wrist angles matched as well. Audio cue is used to indicate a successful target match. The dashed curve shows the trajectory of the hand movement. Some DOFs of the arm are fixed for simplicity.

FIG. 15. The hand reaching exercise designed to improve voluntary motor control. The shoulder, elbow and wrist angles are displayed in real-time (represented by the brown, blue and red circles, respectively). The subject is asked to move the hand from the current position (the green circle) to the target (the red dot) by placing the green circle around the red dot, while keeping the shoulder, elbow and wrist angles matched as well. Audio cue is used to indicate a successful target match. The target in left figure represents a flexed arm position, while the one on the right corresponds to an extended arm position. The light red line shows the trajectory of the hand movement. Some DOFs of the arm are fixed for simplicity.

With the workspace in the horizontal plane determined by diagnosis for an individual patient in the diagnosis, a number of target points in the workspace can be displayed and the patient is asked to move the hand from the current position to the target, while matching the individual joint angles as well. A circle in the virtual hand needs to overlap the red-dot target on the computer monitor for a successful match (FIG. 15). Assistance (or resistance) can be provided by the apparatus to the impaired arm during the voluntary movement training when needed. Once a target is reached, it becomes the new current position and a new target in the workspace is displayed for the subject to move to form the new current position (FIG. 15). The shoulder external rotation, flexion, forearm supination can be fixed for simplicity but they can be represented in the figure and matched by the subject if needed). The patients perform the voluntary exercise for about 20 minutes.

For potential further development, as the patient progresses in motor control capability, the workspace is increased and resistance instead of assistance may be provided during the movement to make it more challenging to the patients.

D. To Evaluate the Outcome in Terms of the Biomechanical Properties and Motor-Control Ability Induced by the Passive Stretching and Active Movement Exercise at the Multiple Joints Involved, Including the Passive Range of Motion (ROM) and Stiffness at Each Joint, Passive Arm ROM, Coupling Torques/Stiffness Between the Joints/DOFs, Active ROM at Each Joint and Coupled Movement at the Other Joints, Hand Reaching Workspace, Reaching Accuracy and Velocity, and Muscle Strength at Each Joints and Coupled Torques at Other Joints.

D.1. Procedure

For evaluation of the stretching and active movement treatments, a number of biomechanical measures is obtained.

The subject sits upright with the shoulder, elbow and wrist axes aligned with the corresponding motor and long axis of the forearm concentric with the supination circular guide (FIG. 1). The initial position is 60° horizontal adduction for the shoulder, and 60°, 25° and 60° for the elbow flexion, wrist flexion, and forearm supination, respectively (FIG. 1).

At the beginning and end of the treatment, passive stretching is done at matched low terminal torques and slow velocity to evaluate the passive ROM (a direct measure of contracture) and stiffness of each of the joints (shoulder horizontal abduction, elbow and wrist flexion), and cross coupling torques between the shoulder, elbow and wrist. Moving into joint extreme positions manifests the passive mechanical changes in muscles-joints, while the very slow speed controlled by the servomotor minimizes reflex contributions. Reversing the rotation at a common resistance torque level allows objective and accurate comparisons between before and after stretching. The robot moves one of the joints slowly until a prespecified resistance torque is reached at this target joint while holding the other joints at their initial positions. Joint angle and multi-axis torques are recorded at the shoulder, elbow and wrist joints simultaneously. The same test is repeated without holding the other joints. The procedure is repeated for each of the multi-joints and multi-DOFs.

Identifying Dynamics of a Limb with Multiple Joints/DOFs

Multi-joint and multi-DOF dynamics of the human arm can be described quantitatively using the rehabilitation robot and the system parameters evaluated can be used for the diagnosis and evaluations described in this invention. The dynamics of arm with the shoulder, elbow and wrist moving in the horizontal plane will be used as an example and described in detail below. As the shoulder, elbow and wrist are controlled by the robot and rotate in the horizontal plane with three DOFs, the relationships between the shoulder, elbow and wrist torques (system inputs) and the shoulder, elbow and wrist angles (system outputs) can be derived through Lagrange-Euler or Newton-Euler formulations. The torques about the vertical axes at the shoulder, elbow and wrist are composed of the inertial, viscous, elastic, Coriolis, and centripetal components. Considering the total torques at each joint are summations of the individual torque components, three-joint dynamics can be described as:

$$\begin{bmatrix} I_{11} & I_{12} & I_{13} \\ I_{21} & I_{22} & I_{23} \\ I_{31} & I_{32} & I_{33} \end{bmatrix} \begin{bmatrix} \Delta\ddot{\phi}_1(t) \\ \Delta\ddot{\phi}_2(t) \\ \Delta\ddot{\phi}_3(t) \end{bmatrix} + \begin{bmatrix} B_{11} & B_{12} & B_{13} \\ B_{21} & B_{22} & B_{23} \\ B_{31} & B_{32} & B_{33} \end{bmatrix} \begin{bmatrix} \Delta\dot{\phi}_1(t) \\ \Delta\dot{\phi}_2(t) \\ \Delta\dot{\phi}_3(t) \end{bmatrix} + \quad (2)$$

$$\begin{bmatrix} K_{11} & K_{12} & K_{13} \\ K_{21} & K_{22} & K_{23} \\ K_{31} & K_{23} & K_{33} \end{bmatrix} \begin{bmatrix} \Delta\phi_1(t) \\ \Delta\phi_2(t) \\ \Delta\phi_3(t) \end{bmatrix} + \begin{bmatrix} C_{11} & C_{12} & C_{13} & C_{14} & C_{15} & C_{16} \\ C_{21} & C_{22} & C_{23} & C_{24} & C_{25} & C_{26} \\ C_{31} & C_{32} & C_{33} & C_{34} & C_{35} & C_{36} \end{bmatrix}$$

$$\begin{bmatrix} \Delta\dot{\phi}_1^2(t) & \Delta\dot{\phi}_2^2(t) & \Delta\dot{\phi}_3^2(t) & \Delta\dot{\phi}_1(t)\Delta\dot{\phi}_2(t) & \Delta\dot{\phi}_1(t)\Delta\dot{\phi}_3(t) & \Delta\dot{\phi}_2(t)\Delta\dot{\phi}_3(t) \end{bmatrix}^T =$$

$$\begin{bmatrix} \Delta T_1(t) \\ \Delta T_2(t) \\ \Delta T_3(t) \end{bmatrix} + \begin{bmatrix} \xi_1(t) \\ \xi_2(t) \\ \xi_3(t) \end{bmatrix}$$

where $\Delta T_1(t)$, $\Delta T_2(t)$ and $\Delta T_3(t)$ are the measured shoulder, elbow and wrist torque perturbations respectively, $\Delta\phi_1(t)$, $\Delta\phi_2(t)$ and $\Delta\phi_3(t)$ are the angular perturbations of the shoulder, elbow and wrist, respectively. $\xi_1(t)$, $\xi_2(t)$ and $\xi_3(t)$ are the modeling errors. Matrices $[I_{ij}]$, $[B_{ij}]$ and $[K_{ij}]$ represent the inertial, viscous and elastic properties, respectively. The left and right halves of $[C_{ij}]$ describe the nonlinear centripetal and Coriolis effects, respectively. Notice that the Coriolis and centripetal torques are only part of the coupling torques between the two joints. The I, B, and K matrices also characterize couplings between the joints. When the evaluation is done around an operating state, parameters such as $I_{11}$, and $K_{22}$ can be regarded as constants.

From the system dynamics, simplifications can be made in Eq. (1) considering that $C_{34}=2C_{32}$, $C_{25}=C_{26}=-2C_{32}$, $C_{23}=-C_{32}$, $C_{12}=-C_{21}$, $C_{13}=-C_{31}$, $C_{16}=C_{15}=2C_{13}=-2C_{31}$, $C_{14}=2C_{12}=-2C_{21}$ and that the inertia matrix $I_{3\times 3}$ is symmetric. Therefore, Eq. (2) can be simplified as:

$$\begin{bmatrix} I_{11} & I_{21} & I_{31} \\ I_{21} & I_{22} & I_{32} \\ I_{31} & I_{32} & I_{33} \end{bmatrix} \begin{bmatrix} \Delta\ddot{\phi}_1(t) \\ \Delta\ddot{\phi}_2(t) \\ \Delta\ddot{\phi}_3(t) \end{bmatrix} + \begin{bmatrix} B_{11} & B_{12} & B_{13} \\ B_{21} & B_{22} & B_{23} \\ B_{31} & B_{32} & B_{33} \end{bmatrix} \begin{bmatrix} \Delta\dot{\phi}_1(t) \\ \Delta\dot{\phi}_2(t) \\ \Delta\dot{\phi}_3(t) \end{bmatrix} + \quad (3)$$

$$\begin{bmatrix} K_{11} & K_{12} & K_{13} \\ K_{21} & K_{22} & K_{23} \\ K_{31} & K_{32} & K_{33} \end{bmatrix}$$

$$\begin{bmatrix} \Delta\phi_1(t) \\ \Delta\phi_2(t) \\ \Delta\phi_3(t) \end{bmatrix} + \begin{bmatrix} 0 & -C_{21} & -C_{31} & -2C_{21} & -2C_{31} & -2C_{31} \\ C_{21} & 0 & -C_{32} & 0 & -2C_{32} & -2C_{32} \\ C_{31} & C_{32} & 0 & 2C_{32} & 0 & 0 \end{bmatrix}$$

$$\begin{bmatrix} \Delta\dot{\phi}_1^2(t) & \Delta\dot{\phi}_2^2(t) & \Delta\dot{\phi}_3^2(t) & \Delta\dot{\phi}_1(t)\Delta\dot{\phi}_2(t) & \Delta\dot{\phi}_1(t)\Delta\dot{\phi}_3(t) & \Delta\dot{\phi}_2(t)\Delta\dot{\phi}_3(t) \end{bmatrix}^T =$$

$$\begin{bmatrix} \Delta T_1(t) \\ \Delta T_2(t) \\ \Delta T_3(t) \end{bmatrix} + \begin{bmatrix} \xi_1(t) \\ \xi_2(t) \\ \xi_3(t) \end{bmatrix}$$

The off-diagonal elements of the $[B_{ij}]$ and $[K_{ij}]$ matrices characterize the viscous and elastic cross-couplings between the joints, which may be changed significantly by the impairment and will be evaluated to diagnose abnormal cross-couplings in the impaired arm.

Although the system dynamics in Eq. (2) is very complex, an innovative procedure is used here to decompose the complex and almost intractable system to single-joint level, which can then be solved with well established methods.

Eq. (2) above provides a comprehensive characterization of the multi-joint biomechanical properties, such as the cross couplings characterized by the off-diagonal elements of the stiffness matrix [K] and diagonal elements characterize the local stiffness of each individual joint (shoulder, elbow, wrist). Evaluations based on stiffness matrix [K] and viscosity matrix [B] will be valuable in evaluating the impairment and in guiding the rehabilitation.

However, even with simplification, the nonlinear multi-input multi-output system in Eq. (3) still has 27 parameters and is very difficult to identify reliably. The following systematic procedure is developed to identify this complex system (and other complex systems with even more joints/DOFs involved) robustly.

1. When the shoulder joint is perturbed by the robot with the elbow and wrist held at fixed positions, $\phi_2(t)$ and $\phi_3(t)$ are constant; $\Delta\phi_2(t)=\Delta\phi_3(t)=\Delta\dot{\phi}_2(t)=\Delta\dot{\phi}_3(t)=\Delta\ddot{\phi}_2(t)=\Delta\ddot{\phi}_3(t)=0$. The first to third rows of Eq. (3) are reduced to Eq. (3) to (5), respectively. $T_{11}(t)$, $T_{21}(t)$ and $T_{31}(t)$ represent the shoulder, elbow and wrist torques measured in this case, respectively ($\Delta T_{11}(t)$, $\Delta T_{21}(t)$ and $\Delta T_{31}(t)$ correspond to their changes from the initial values). At the shoulder joint, $$I_{11}\Delta\ddot{\phi}_1(t)+B_{11}\Delta\dot{\phi}_1(t)+K_{11}\Delta\phi_1(t)=\Delta T_{11}(t) \quad (4)$$

Parameters $I_{11}$, $B_{11}$ and $K_{11}$ (shoulder inertia, viscosity and stiffness respectively) can be estimated from Eq. (4).

For the elbow joint, the elbow joint torque induced by perturbation at the shoulder gives $$I_{21}\Delta\ddot{\phi}_1(t)+B_{21}\Delta\dot{\phi}_1(t)+K_{21}\Delta\phi_1(t)+C_{21}\Delta\dot{\phi}_1^2(t)=\Delta T_{21}(t) \quad (5)$$

Parameters $I_{21}$, $B_{21}$, $K_{21}$ and $C_{21}$ can be estimated from the above equation. Note that the off-axis terms $B_{21}$ and $K_{21}$ are non-zero due to the viscoelastic coupling between the joints. $B_{21}$ and $K_{21}$ give the viscous and elastic cross-couplings from the shoulder perturbation to the coupled elbow torque, respectively.

For the wrist joint, the wrist joint torque induced by perturbation at the shoulder gives $$I_{31}\Delta\ddot{\phi}_1(t)+B_{31}\Delta\dot{\phi}_1(t)+K_{31}\Delta\phi_1(t)+C_{31}\Delta\dot{\phi}_1^2(t)=\Delta T_{31}(t) \quad (6)$$

Parameters $I_{31}$, $B_{31}$, $K_{31}$, and $C_{31}$ can be estimated from the above equation. Similarly, $B_{31}$ and $K_{31}$ are non-zero due to the viscoelastic coupling between the joints. $B_{31}$ and $K_{31}$ give the viscous and elastic cross-couplings from the shoulder perturbation to the coupled wrist torque, respectively.

2. When the elbow joint is perturbed with the shoulder and wrist held at fixed positions, $\phi_1(t)$ and $\phi_3(t)$ are constant; $\Delta\phi_1(t)=\Delta\phi_3(t)=\Delta\dot{\phi}_1(t)=\Delta\dot{\phi}_3(t)=\Delta\ddot{\phi}_1(t)=\Delta\ddot{\phi}_3(t)=0$. The first to third rows of Eq. (3) are reduced to Eq. (7) to (9), respectively. $T_{12}(t)$, $T_{22}(t)$ and $T_{32}(t)$ represent the shoulder, elbow and wrist torques in this case, respectively. At the shoulder joint, $$I_{12}\Delta\ddot{\phi}_2(t)+B_{12}\Delta\dot{\phi}_2(t)+K_{12}\Delta\phi_2(t)+C_{12}\Delta\dot{\phi}_2^2(t)=\Delta T_{12}(t) \quad (7)$$

Parameters $I_{12}$, $B_{12}$, $K_{12}$, and $C_{12}$ can be estimated from the above equation. Notice that since $I_{12}=I_{21}$, as an option, we can estimate $I_{12}$ from Eq. (5) and substitute it here in Eq. (7) as known for simplification. Similarly, since $C_{12}=-C_{21}$, $C_{12}$ can be estimated from Eq. (5) and taken as known here. $B_{12}$ and $K_{12}$ give the viscous and elastic cross-couplings from the elbow perturbation to the coupled shoulder torque, respectively.

For the elbow joint, the elbow joint torque induced by perturbation at the elbow gives $$I_{22}\Delta\ddot{\psi}_2(t)+B_{22}\Delta\dot{\psi}_2(t)+K_{22}\Delta\psi_2(t)=\Delta T_{22}(t) \quad (8)$$

Parameters I22, B22 and K22 can be estimated from the above equation.

For the wrist joint, the wrist joint torque induced by perturbation at the elbow gives $$I_{32}\Delta\ddot{\phi}_2(t)+B_{32}\Delta\dot{\phi}_2(t)+K_{32}\Delta\phi_2(t)+C_{32}\Delta\dot{\phi}_2^2(t)=\Delta T_{32}(t) \quad (9)$$

Parameters $I_{32}$, $B_{32}$, $K_{32}$, and $C_{32}$ can be estimated from the above equation. $B_{32}$ and $K_{32}$ give the viscous and elastic cross-couplings from the elbow perturbation to the coupled wrist torque, respectively.

An example of estimating parameters of the multi-joint/multi-DOF system dynamics is given here.

To evaluate the multi-joint biomechanical changes post stroke, elements of the stiffness $[K_{ij}]$ matrix are determined (see Eq. (2) and Eq. (3)) with the off-diagonal elements characterizing the cross-coupling stiffness between the joints and the diagonal elements characterizing elastic stiffness local to the individual joints. Similarly, the off-diagonal elements of the $[B_{ij}]$ matrix are estimated for the cross-coupling viscous components between joints and the diagonal elements for viscosity local to the shoulder, elbow or wrist. The robotic arm moves an individual joint selectively with the multi-axis torques and angles measured at all the joints simultaneously. With the joint movement well controlled by the robot, the $[K_{ij}]$ and $[B_{ij}]$ can be estimated quantitatively based on above equations (one equation at a time so the complex system is reduced to the single-joint level).

Figure 16:
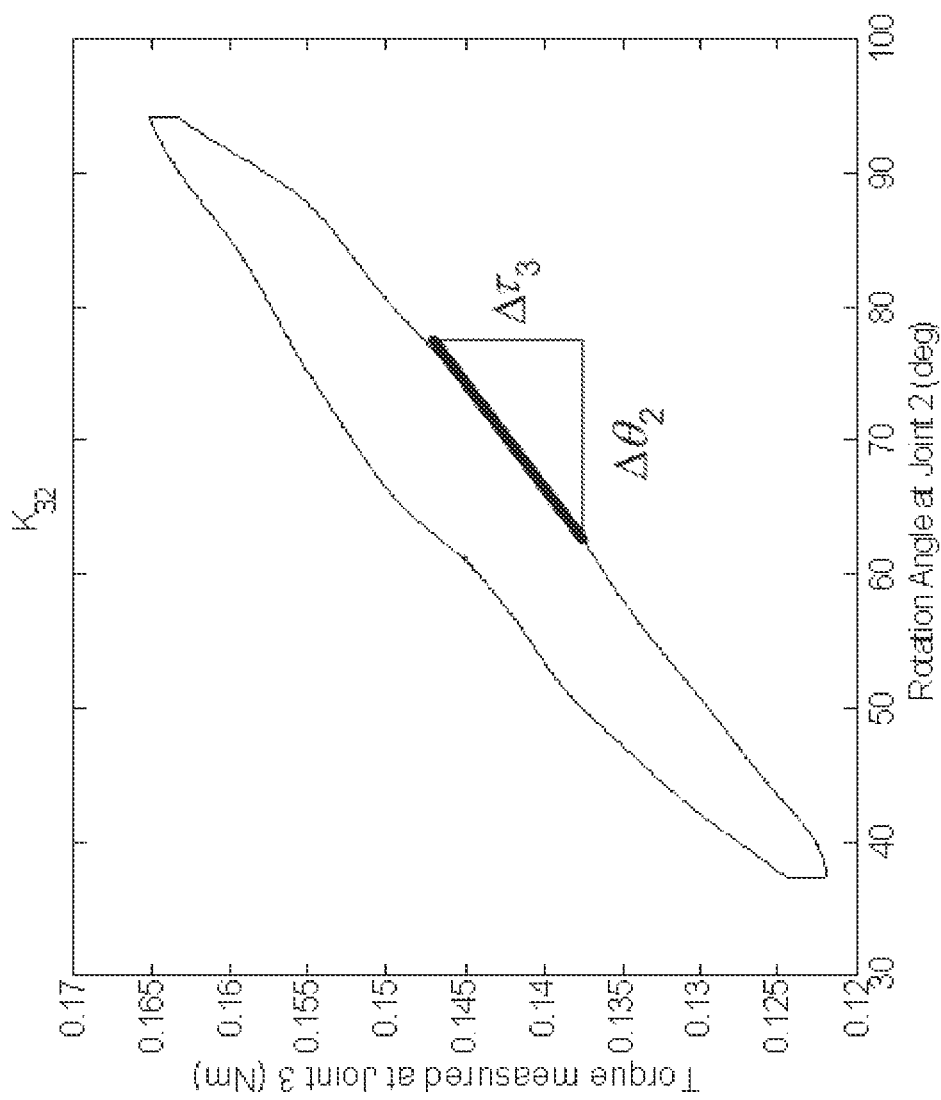
FIG. 16 is a graphic display of a cross joint torque-angle relationship. The elbow is moved by the robot with the wrist joint held by the robot. The cross-joint stiffness K32 is evaluated as the slope of the loading phase of the curve relating the wrist flexion torque to the elbow flexion angle.

The multi-joint/multi-DOF stiffness matrix K can be determined quantitatively using the rehabilitation robot. For example, $K_{32}$ in Eq. (9) can be determined as the slope of curve between the wrist torque and elbow angle when the elbow is moved by the rehabilitation robot with the wrist locked by the robot and torque measured (FIG. 16). The stiffness matrix K for the passive shoulder-elbow-wrist joints is determined from multiple stroke survivors and multiple healthy subjects using the robot arm. Stroke survivors showed not only much increased stiffness at the shoulder, elbow and wrist locally but also much higher cross couplings among the joints (FIG. 17).

The controller disclosed above is either loaded with the dynamics data structure above or may interface with the data structure recorded in a machine readable format.

FIG. 16. Cross-joint torque-angle relationship. The elbow is moved by the robot with the wrist joint held by the robot. The cross-joint stiffness $K_{32}$ is evaluated as the slope of the loading phase of the curve relating the wrist flexion torque to the elbow flexion angle.

Figure 17:
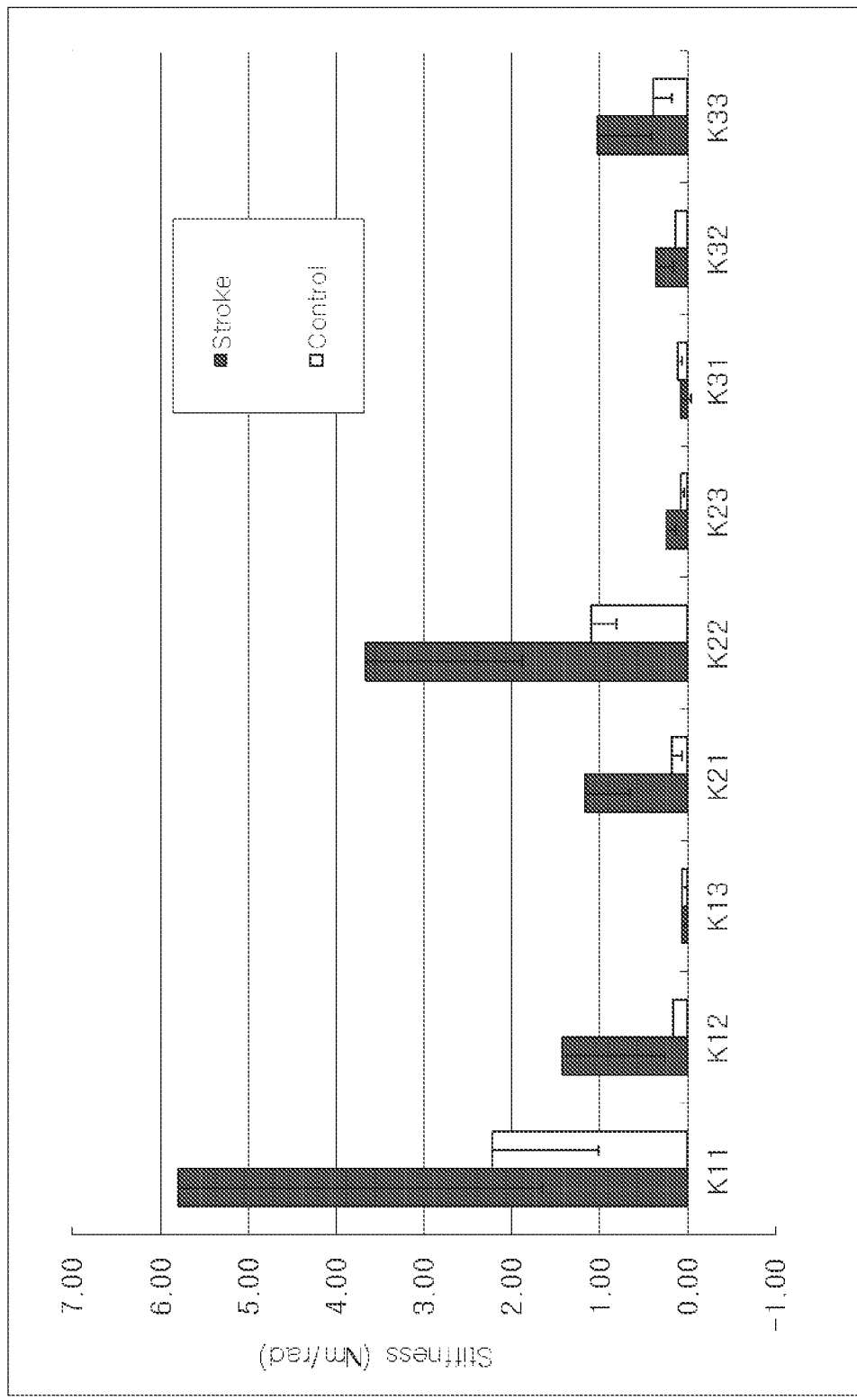
FIG. 17 is a graphic display of stiffness matrix. Diagonal and off-diagonal elements of stiffness matrix [K] from 7 stroke survivors and 3 healthy subjects. Subscripts 1, 2 and 3 correspond to the shoulder, elbow and wrist, respectively. The standard deviation bars are only shown in one direction for clarity.

FIG. 17. Diagonal and off-diagonal elements of stiffness matrix [K] from 7 stroke survivors and 3 healthy subjects. Subscripts 1, 2 and 3 correspond to the shoulder, elbow and wrist, respectively. The standard deviation bars are only shown in one direction for clarity.

Impairments during voluntary movement can also be quantified by the rehabilitation robot, which can be used for the diagnosis and outcome evaluations. Impairment in independent control of individual joint (so-called loss of individuation) can be evaluated quantitatively and systematically by analyzing the coupled torque/movement at the other joints/DOFs when the subject is asked to move a target joint selectively without moving the others. As an example of characterization of loss of individuation, the coupled elbow torque during shoulder horizontal abduction is shown in FIG. 18(a) for 4 stroke survivors and one healthy subject. The corresponding motor status score (a measure of human arm motor function) of the patients is shown in FIG. 18(b).

Figure 18:
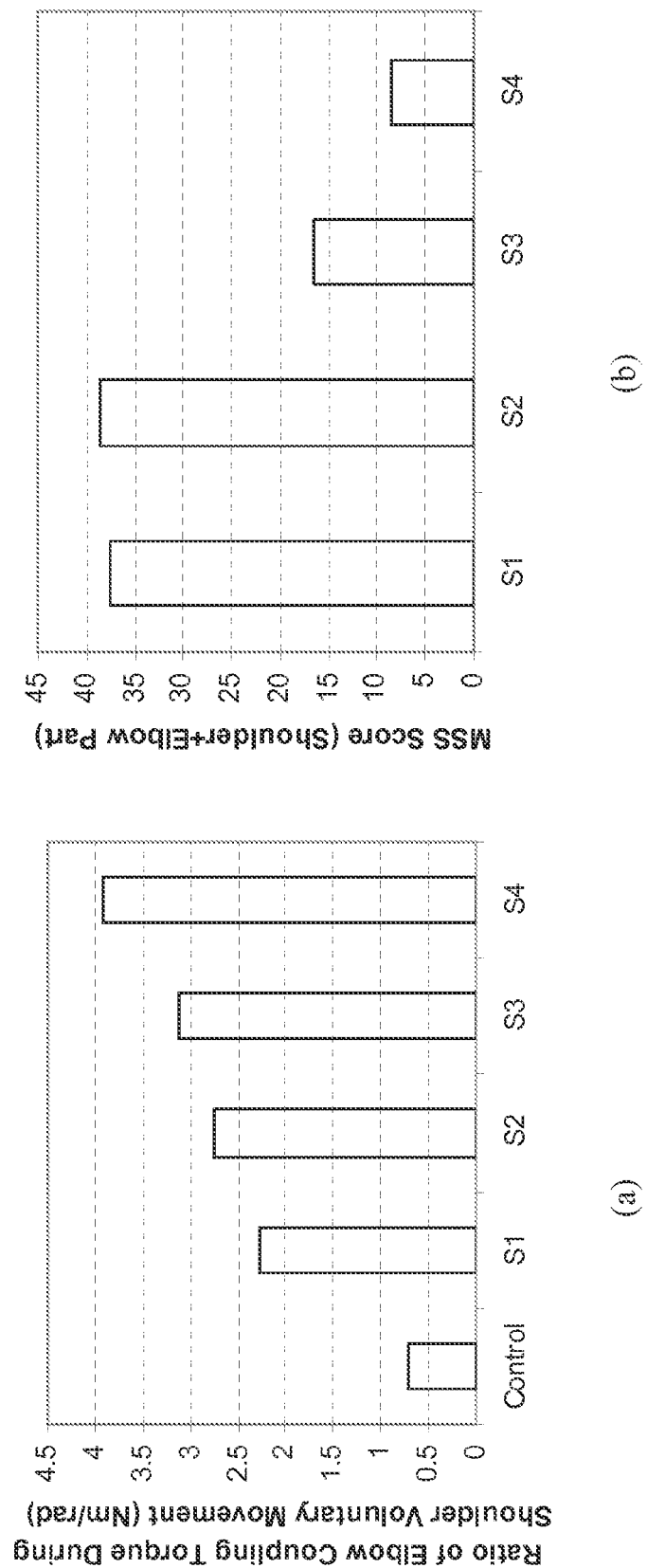
FIG. 18 is a graphic display of a motor status S over. (a) Loss of individuation characterized by the peak coupled torque at the elbow (flexion/extension) when the subject tried to move the shoulder isolately in horizontal abduction. S1, S2, S3 and S4 represent four stroke survivors. (b) The corresponding motor status score of the four stroke survivors, which is negatively related to the cross-joint couplings.

FIG. 18. (a) Loss of individuation characterized by the peak coupled torque at the elbow (flexion/extension) when the subject tried to move the shoulder isolately in horizontal abduction. S1, S2, S3 and S4 represent four stroke survivors. (b) The corresponding motor status score of the four stroke survivors, which is negatively related to the cross-joint couplings.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A human interface machine comprising:
    an arm brace having a temporary attachment element adapted to temporarily attach a human arm; the arm brace disposed to move with the human arm while attached and jointed such that an arm joint can move through a first degree of freedom and at least one other degree of freedom;
    a scapular elevation apparatus that includes a shoulder platform;
    a shoulder joint pivotally coupled to the scapular elevation apparatus that includes a shoulder force/torque sensor, and a shoulder abduction motor, the shoulder force/torque sensor positioned to measure six degrees of freedom;
    an upper arm length adjustment affixed to the shoulder joint;
    an elbow joint affixed to the upper arm length adjustment including an elbow motor and an elbow force/torque sensor;
    a forearm length adjustment affixed to the elbow joint;
    a wrist and hand part affixed to the forearm length adjustment including a supination/pronation motor, a wrist flexion/extension motor, a wrist force/torque sensor, a hand opening/closing motor, and a metacarpophalangeal joint torque sensor;
    the plurality of sensors in operative communication with the arm brace such that at least one sensor senses a first force when an arm joint is driven in a first degree of freedom and such that the same sensor senses a second force when the arm joint is driven in a second degree of freedom; and
    a processor in operative communication with the plurality of sensors and the plurality of motors, the processor configured to calculate a coupling relationship between a movement in the first degree of freedom and the second force sensed in the second degree of freedom, the processor further configured to drive the arm joint through a first degree of motion.

2. The machine of claim 1, wherein the first force includes a torque component; and the second force includes a torque component.

3. The machine of claim 2, wherein the coupling relationship is between the torque component of the first force and the torque component of the second force.

4. The machine of claim 3, wherein the torque components are, individually, selected from the group consisting of inertial, viscous, elastic, Coriolis and centripetal components.

5. The machine of claim 3, wherein a peak coupling torque is calculated.

6. The machine of claim 1, wherein said human interface machine is a rehabilitation robot.

7. The machine of claim 1, wherein the plurality of motors are disposed to drive the arm brace through said first degree of freedom and through the second degree of freedom.

8. The machine of claim 7, wherein said human interface machine is further configured to move in said degrees of freedom in either an active mode or a passive mode.

9. The machine of claim 7 wherein said processor is configured to set a range of motion limit, said range of motion limit being a maximum torque for said first degree of freedom.

10. The machine of claim 7, wherein the coupling relationship sums said torque components.

11. The machine of claim 7, wherein said processor is configured to control a speed of a motion through a said first degree of freedom according to said coupling relationship.

12. The machine of claim 1, wherein the coupling relationship is an Euler formulation.

13. The machine of claim 12, wherein the coupling relationship assigns to off diagonal elements a cross-coupling stiffness between the arm joints and assigns a diagonal element and elastic stiffness local to an individual arm joint.

14. The machine in claim 1, wherein the processor is configured to calculate the coupling relationship according to the following formula:

$$\begin{bmatrix} I_{11} & I_{12} & I_{13} \\ I_{21} & I_{22} & I_{23} \\ I_{31} & I_{32} & I_{33} \end{bmatrix} \begin{bmatrix} \Delta\ddot{\phi}_1(t) \\ \Delta\ddot{\phi}_2(t) \\ \Delta\ddot{\phi}_3(t) \end{bmatrix} + \begin{bmatrix} B_{11} & B_{12} & B_{13} \\ B_{21} & B_{22} & B_{23} \\ B_{31} & B_{32} & B_{33} \end{bmatrix} \begin{bmatrix} \Delta\dot{\phi}_1(t) \\ \Delta\dot{\phi}_2(t) \\ \Delta\dot{\phi}_3(t) \end{bmatrix} + \quad (2)$$

$$\begin{bmatrix} K_{11} & K_{12} & K_{13} \\ K_{21} & K_{22} & K_{23} \\ K_{31} & K_{23} & K_{33} \end{bmatrix} \begin{bmatrix} \Delta\phi_1(t) \\ \Delta\phi_2(t) \\ \Delta\phi_3(t) \end{bmatrix} + \begin{bmatrix} C_{11} & C_{12} & C_{13} & C_{14} & C_{15} & C_{16} \\ C_{21} & C_{22} & C_{23} & C_{24} & C_{25} & C_{26} \\ C_{31} & C_{32} & C_{33} & C_{34} & C_{35} & C_{36} \end{bmatrix}$$

$$\begin{bmatrix} \Delta\dot{\phi}_1^2(t) & \Delta\dot{\phi}_2^2(t) & \Delta\dot{\phi}_3^2(t) & \Delta\dot{\phi}_1(t)\Delta\dot{\phi}_2(t) & \Delta\dot{\phi}_1(t)\Delta\dot{\phi}_3(t) & \Delta\dot{\phi}_2(t)\Delta\dot{\phi}_3(t) \end{bmatrix}^T =$$

$$\begin{bmatrix} \Delta T_1(t) \\ \Delta T_2(t) \\ \Delta T_3(t) \end{bmatrix} + \begin{bmatrix} \xi_1(t) \\ \xi_2(t) \\ \xi_3(t) \end{bmatrix}$$

where $\Delta T_1(t)$, $\Delta T_2(t)$ and $\Delta T_3(t)$ are measured shoulder, elbow and wrist torque perturbations respectively, $\Delta\phi_1(t)$, $\Delta\phi_2(t)$ and $\Delta\phi_3(t)$ are angular perturbations of the shoulder, elbow and wrist, respectively, $\xi_1(t)$, $\xi_2(t)$, and $\xi_3(t)$ are modeling errors, matrices [Iij], [Bij] and [Kij] represent the inertial, viscous and elastic properties, respectively, and the left and right halves of [Cij] describe the nonlinear centripetal and Coriolis effects, respectively.

15. The machine of claim 14, wherein the processor is configured to calculate the coupling relationship according to an equation selected from the group consisting of:

$I_{11}\Delta\ddot{\phi}_1(t)+B_{11}\Delta\dot{\phi}_1(t)+K_{11}\Delta\phi_1(t)=\Delta T_{11}(t)$, $I_{21}\Delta\ddot{\phi}_1(t)+B_{21}\Delta\dot{\phi}_1(t)+K_{21}\Delta\phi_1(t)+C_{21}\Delta\dot{\phi}_1^2(t)=\Delta T_{21}(t)$, and $I_{31}\Delta\ddot{\phi}_1(t)+B_{31}\Delta\dot{\phi}_1(t)+K_{31}\Delta\phi_1(t)+C_{31}\Delta\dot{\phi}_1^2(t)=\Delta T_{31}(t)$ where I is joint inertia, B is joint viscosity and K is joint stiffness.

16. The machine of claim 14, wherein the processor is configured to calculate the coupling relationship according to an equation selected from the group consisting of:

$I_{12}\Delta\ddot{\phi}_2(t)+B_{12}\Delta\dot{\phi}_2(t)+K_{12}\Delta\phi_2(t)+C_{12}\Delta\dot{\phi}_2^2(t)=\Delta T_{12}(t)$, $I_{22}\Delta\ddot{\psi}_2(t)+B_{22}\Delta\dot{\psi}_2(t)+K_{22}\Delta\psi_2(t)=\Delta T_{22}(t)$, and $I_{32}\Delta\ddot{\phi}_2(t)+B_{32}\Delta\dot{\phi}_2(t)+K_{32}\Delta\phi_2(t)+C_{32}\Delta\dot{\phi}_2^2(t)=\Delta T_{32}(t)$, where I is joint inertia, B is joint viscosity and K is joint stiffness.

17. The machine of claim 1, wherein the processor is configured to control one of the plurality of motors to execute passive stretching done at matched low terminal torques and/or to slow velocity.

18. The machine of claim 1, wherein the processor is configured to move a joint to a first range of motion limit in a first degree of freedom and then hold that position until a second range of motion limit is reached in motion along a second degree of freedom.

19. The machine of claim 1, wherein the processor is configured to move one of the plurality of motors at higher velocity through a central portion of a range of motion and at a slower velocity in a portion of said range of motion adjacent to a range of motion limit.

20. The machine of claim 1, wherein the plurality of sensors are configured to simultaneously measure said forces.

21. The machine of claim 1 wherein said machine is used to treat patients according to steps comprising:
 executing a multi-joint/multi degree of freedom diagnosis;
 executing a passive stretching treatment;
 executing a voluntary movement training; and
 evaluating an outcome using said machine of claim 1.

* * * * *